United States Patent
Beumer et al.

(10) Patent No.: US 9,393,225 B2
(45) Date of Patent: Jul. 19, 2016

(54) MELANOMA CHEMOPREVENTION

(71) Applicant: University of Pittsburgh—Of the Commonwealth System of Higher Education, Pittsburgh, PA (US)

(72) Inventors: Jan H. Beumer, Aspinwall, PA (US); John M. Kirkwood, Gibsonia, PA (US); Shivendra V. Singh, Wexford, PA (US); Charles K. Brown, Genoa City, WI (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 10 days.

(21) Appl. No.: 14/398,713

(22) PCT Filed: May 3, 2013

(86) PCT No.: PCT/US2013/039518
§ 371 (c)(1),
(2) Date: Nov. 3, 2014

(87) PCT Pub. No.: WO2013/166421
PCT Pub. Date: Nov. 7, 2013

(65) Prior Publication Data
US 2015/0141507 A1    May 21, 2015

Related U.S. Application Data

(60) Provisional application No. 61/643,098, filed on May 4, 2012.

(51) Int. Cl.
*A61K 31/26* (2006.01)
(52) U.S. Cl.
CPC .................................... *A61K 31/26* (2013.01)
(58) Field of Classification Search
CPC ...................................................... A61K 31/26
USPC ........................................................ 514/514
See application file for complete search history.

(56) References Cited

U.S. PATENT DOCUMENTS

| 5,411,986 A | 5/1995 | Cho et al. |
| 2011/0014137 A1 | 1/2011 | Talalay et al. |

OTHER PUBLICATIONS

Goldstein, et al. "Association of MC1R variants and risk of melanoma in melanoma-prone families with CDKN2A mutations." *Cancer Epidemiology Biomarkers & Prevention* vol. 14, No. 9 (2005): pp. 2208-2212.
Hahm, et al. "Sulforaphane inhibits constitutive and interleukin-6-induced activation of signal transducer and activator of transcription 3 in prostate cancer cells." *Cancer Prevention Research* vol. 3, No. 4 (2010): pp. 484-494.
Hamsa, et al. "Induction of apoptosis by sulforaphane in highly metastatic B16F-10 melanoma cells." *Drug and Chemical Toxicology* vol. 34, No. 3 (2011): pp. 332-340.
Messina, et al. "Activated stat-3 in melanoma." *Cancer Control* vol. 15, No. 3 (2008): pp. 196-201.
Misiewicz, et al. "Sulforaphane and 2-oxohexyl isothiocyanate induce cell growth arrest and apoptosis in L-1210 leukemia and ME-18 melanoma cells." *Oncology Reports* vol. 10, No. 6 (2003): pp. 2045-2050.
Russo, et al. "Phytochemicals in cancer prevention and therapy: truth or dare?" *Toxins* vol. 2, No. 4 (2010): pp. 517-551.
Thejass, et al. "Modulation of cell-mediated immune response in B16F-10 melanoma-induced metastatic tumor-bearing C57BL/6 mice by sulforaphane." *Immnunopharnmacology and Immunotoxicology* vol. 29, No. 2 (2007): pp. 173-186.
Wang, et al. "STAT3 as a biomarker of progression in atypical nevi of patients with melanoma: dose-response effects of systemic IFNα therapy." *Journal of Investigative Dermatology* vol. 128, No. 8 (2008): pp. 1997-2002.
Wei, et al. "Mechanism of sulforaphane-induced growth arrest and apoptosis in SK-MEL-31 melanoma cells." *Proceedings of the American Association for Cancer Research* vol. 47 (2006): p. 1316.

*Primary Examiner* — Raymond Henley, III
(74) *Attorney, Agent, or Firm* — Klarquist Sparkman, LLP

(57) ABSTRACT

Disclosed herein are methods and uses for preventing melanoma, reducing progression of atypical nevi, and inducing cell cycle arrest and/or apoptosis in a melanoma cell through oral and enteral administration of sulforaphane to subjects indicated to be at risk due to factor(s) such as medical history of atypical nevi, melanoma, or UV exposure. Sulforaphane can be administered orally as a safe and well-tolerated natural agent as a chemopreventive strategy in individuals with atypical melanocytic nevi.

22 Claims, 12 Drawing Sheets

FIG. 4A
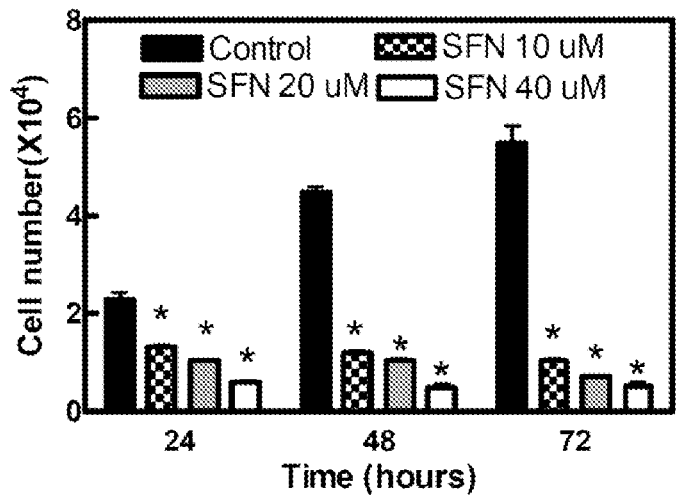
FIG. 4B
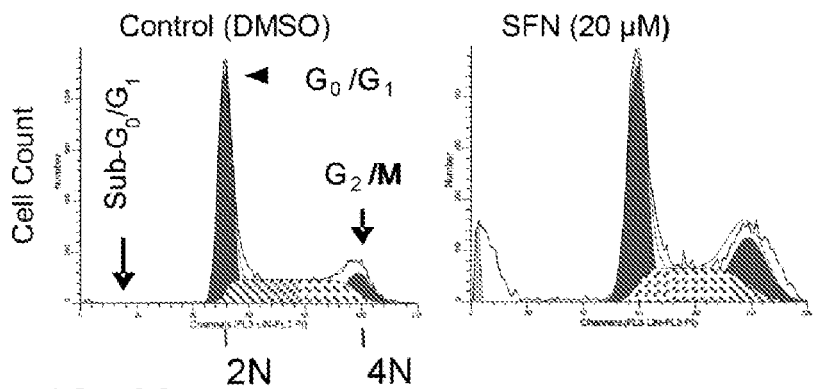
FIG. 4C
| | % Cells in | |
|---|---|---|
| | Control | SFN (20 μM) |
| Sub-$G_0/G_1$ | 0.54• 0.10 | 2.99• 0.22 # |
| $G_0/G_1$ | 47.07• 2.35 | 11.85• 0.35 # |
| S | 15.02• 0.49 | 12.88• 0.68 |
| $G_2/M$ | 36.92• 2.34 | 72.42• 4.22 # |

FIG. 12

| Parameter | Day 1 | Day 2 | Day 28 | Follow-Up 3 Months | Follow-Up 6 Months |
|---|---|---|---|---|---|
| History & Physical | X | | | | |
| Serum Pregnancy Test | X | | | | |
| Complete Blood Count | X | | X | | |
| Complete Metabolic Panel | X | | X | | |
| Abstain From *Brassica* | ▼ | | ▲ | | |
| Fasting | X | X | X | | |
| Photography | X | | X | X | X |
| Excisional Biopsy | X | X | X | | |
| Serum sulforaphane level | X | X | X | | |
| Study Drug Administration | ▼ | | ▲ | | |

MELANOMA CHEMOPREVENTION

CROSS REFERENCE TO RELATED APPLICATIONS

This is a §U.S. national stage of PCT/US2012/039518, filed May 3, 2013, which was published in English under PCT Article 2(2), and claims the benefit of U.S. Provisional Application No. 61/643,098, filed May 4, 2012, which is incorporated by reference herein.

FIELD

This disclosure is related to the use of sulforaphane administered orally for the prevention of melanoma, such as in specific populations of subjects that are at risk for melanoma.

BACKGROUND

Safe and effective chemoprevention agents have enormous potential to improve human health. This was first demonstrated convincingly in cardiovascular disease, where modifiable risk factors such as high blood pressure and elevated cholesterol levels were identified and targeted for pharmacological management. The result has been the reduction of both the morbidity and mortality associated with heart disease. For some cancers, the promise of chemoprevention has already been realized. Recurrence of breast cancer is being reduced by treatment with tamoxifen, and the incidence of colon cancer is being reduced significantly with NSAIDs.

Melanoma is less common than other skin cancers, but it is much more dangerous if it is not detected early. Melanoma causes the majority (75%) of deaths related to skin cancer. Worldwide, doctors diagnose about 160,000 new cases of melanoma yearly. The diagnosis is more frequent in women than in men. In women, the most common site is the legs and melanomas in men are most common on the back Melanomas are aggressive and frequently metastatic tumors develop. Melanocytic nevi can be broadly categorized into normal nevocellular nevi (or benign neoplasms of melanocytes) and atypical nevi, which are also known as dysplastic nevi.

Minimizing exposure to sources of ultraviolet radiation, such as from the sun and sunbeds, following sun protection measures, and wearing sun protective clothing can offer protection from melanoma. However, a need remains for further preventive measures, such as to prevent melanoma in subjects that are pre-disposed to develop this disease.

SUMMARY

It is disclosed herein that pharmaceutical compositions including sulforaphane (SFN) can be administered to a subject to reduce progression of atypical nevi and/or to prevent melanoma. The subjects can have atypical nevi, can have a dysplastic nevus syndrome, or can be at risk for developing melanoma, such as due to a family history.

In some embodiments, methods or uses are provided for reducing progression of atypical nevi in a subject. In an example embodiment, a therapeutically effective amount of a pharmaceutical composition including SFN is administered orally to a subject having atypical nevi, thereby reducing progression of the atypical nevi in the subject.

In additional embodiments, methods or uses are provided for preventing melanoma in a subject. In an example embodiment, a therapeutically effective amount of a pharmaceutical composition including SFN is administered orally to a subject having atypical nevi, or otherwise at risk for developing melanoma, thereby preventing melanoma from developing in the subject.

In additional embodiments, methods or uses are provided to induce cell cycle arrest and/or apoptosis of a dysplastic skin cell and/or melanoma cell. In an example embodiment, a pharmaceutical composition including SFN is administered orally to a subject having a melanoma cell, thereby inducing cell cycle arrest and/or apoptosis of the melanoma cell of the subject.

The foregoing and other objects, features, and advantages of the invention will become more apparent from the following detailed description, which proceeds with reference to the accompanying figures.

BRIEF DESCRIPTION OF THE FIGURES

FIGS. 4A-4C are a bar graph (A), plot (B) and table (C) demonstrating the effect of SFN treatment on proliferation of SK-MEL 31 cells. Proliferation was measured by (A) trypan blue dye exclusion assay and (B) FACS cell cycle distribution assay after PI. For trypan blue exclusion assay, SK-MEL 31 cells were exposed to 10, 20 or 40 µM SFN or DMSO (control) for 24, 48 and 72 hours. Data are presented as mean±SE (n=3) from a representative experiment. For cell cycle distribution assay, cells were exposed to 20 µM SFN or DMSO (control) for 24 hours, results were presented as mean±SE (n=3) from a representative experiment. All experiments were repeated at least twice with comparable results. The notation (*) indicates significantly different result compared with control ($p<0.01$) by one way ANOVA, while the notation (#) indicates a significantly different compared with control ($p<0.01$) by Student's t-test.

FIG. 7A shows representative western blots for expression of Bcl-2 family using lysates from SK-MEL 31 cells exposed to 20 μM SFN for specified time intervals. Equal amounts of lysate protein (10 μg for Bax and 40 μg for other molecules) were subjected to gel electrophoresis. FIG. 7B shows Western blot assays of IAPs and Smac, cytochrome c released from mitochondria after SFN treatment. Whole cell lysate were used for cIAP1, XIAP (40 μg for each lane), while cytosolic fraction were prepared for Smac and cytochrome c assay (equal volume of lysate for each lane), the target protein level changes were corrected with corresponding actin level for each lane. All experiments were repeated twice, with comparable results.

FIG. 12 is a table showing scheduled evaluations for subjects evaluated by the protocol presented in FIG. 11.

DESCRIPTION OF EMBODIMENTS

Figure 1:
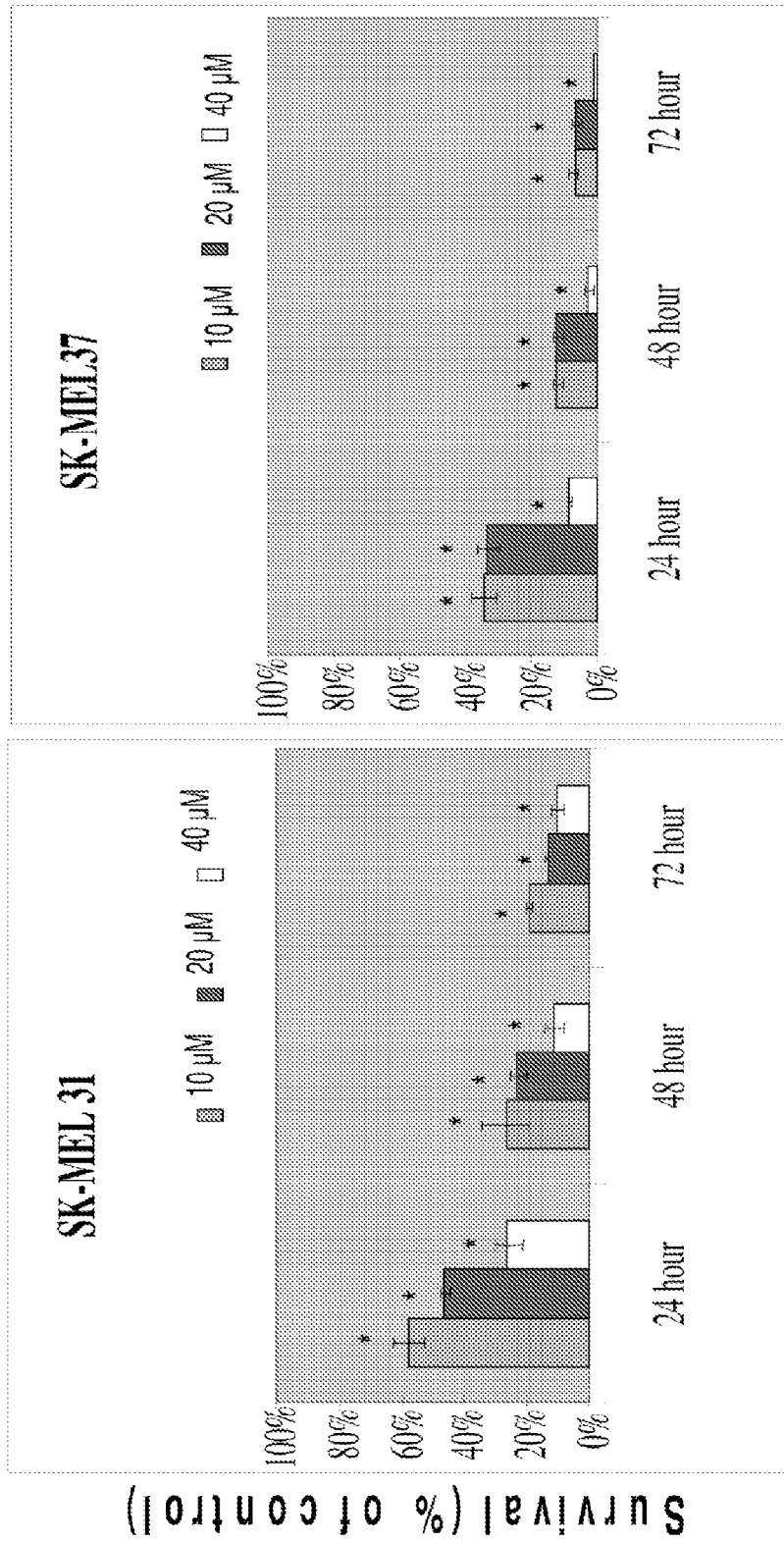
FIG. 1 is a set of bar graphs showing that SFN inhibits melanoma cell growth in vitro.

There is a genetic predisposition to melanoma that requires unique preventive measures. The presence of atypical nevi is positively correlated with increased risk of melanoma and occurs in two main settings. Subjects with familial melanoma or dysplastic nevus syndrome exhibit an autosomal dominant trait with a lifetime melanoma risk approaching 100%. Limiting UV radiation exposure cannot serve as the sole agent of prevention in these individuals.

In light of excellent survival rates for melanoma discovered while still in situ compared to the poorer prognosis associated with more advanced disease, efforts are warranted to identify means of primary prevention of melanoma. Given the continually rising incidence of melanoma, the ineffectiveness of UV radiation protective strategies and prevalence of genetic pre-disposing factors, chemoprevention serves as an attractive strategy for primary prevention of melanoma.

Methods are provided herein for reducing the progression of nevi. Methods are also disclosed for preventing melanoma, including reducing the appearance of melanoma precursor lesions. These methods include the oral administration of Sulforaphane (SFN). Sulforaphane (SFN, 1-isothiocyanato-4-(methylsulfinyl)-butane; $CH_3-SO-(CH_2)_4-N=C=S$), a constituent of cruciferous vegetables including broccoli is generated through catalytic hydrolysis of glucoraphanin by myrosinase, an endogenous enzyme and released upon damage of the plant cells during digestive processing (cutting or chewing). See Zhang et al., Proc. Natl Acad. Sci. USA (1992) 89: 2399-2403. SFN affects biomarkers in the progression from atypical nevi to melanoma. One biomarker is the effect of SFN on the Signal Transducer and Activation of Transcription (STAT) pathways whose dysregulation promotes tumorigenesis in melanoma and other solid tumors. SFN inhibits carcinogenesis through several different mechanisms within the initiation, promotion, and progression phases of cancer development in multiple types of tumors.

SFN can be administered orally as a safe and well-tolerated agent for chemoprevention in individuals with atypical melanocytic nevi which are associated with an increased predisposition towards developing melanoma.

Abbreviations

To facilitate review of the various embodiments of this disclosure, the following explanations of abbreviations are provided:
BSE Broccoli Sprout Extract
C Celsius
CI Confidence interval
ELISA Enzyme-linked immunosorbent assay
FAMM Familial atypical multiple mole-melanoma
h hour(s)
MC1R MelanoCortin 1 Receptor
μM microMole
PD Pharmacodynamics
PK Pharmacokinetics
RIA Radioimmunoas say
SAE rate Small Area Estimate rate
SE Standard Error
SFN Sulforaphane
STAT Signal Transducer and Activation of Transcription
TUNEL Terminal deoxynucleotidyl transferase dUTP Nick End Labeling Terms In order to facilitate review of the various embodiments of the disclosure, the following explanations of specific terms are provided:

Administering: Introducing a pharmaceutical composition to a subject. In one example, a pharmaceutical composition is administered orally. Examples of oral administration include swallowing a liquid, a gel capsule or other pill or other solid.

Animal: Living multi-cellular vertebrate organisms, a category that includes, for example, mammals and birds. The term mammal includes both human and non-human mammals. Similarly, the term "subject" includes both human and veterinary subjects.

Biopsy: A sample collection technique in which tissue is removed from a subject and sent to a pathologist to render a diagnosis. As an example, in a skin biopsy, a portion of the skin of a subject is removed. As an example, a skin biopsy may be performed under local anesthetic. In other examples, a skin biopsy may be a shave biopsy, a punch biopsy, an excisional biopsy, or an incisional biopsy, among others. The vast majority of nevi and melanoma precursor lesions are amenable to visual/photographic identification/documentation and may be biopsied for histopathologic evaluation, as well as for the performance of molecular biologic and immunohistologic testing for candidate markers of progression.

Buccal administration: Administration that involves absorption of a drug through membranes in the mouth.

Chemoprevention: Prophylactic or preventive use of natural or synthetic agents to delay, reverse, suppress or prevent premalignant molecular or histological lesions from progressing to invasive cancer. The concept applies to primary prevention in high-risk individuals, secondary prevention in those with premalignant conditions, and tertiary prevention in aiding those with a cured malignancy from developing a second primary cancer.

A chemopreventive agent is any biological or chemical agent with prophylactic or preventive usefulness in the treatment of diseases characterized by abnormal cell growth. Such diseases include tumors, neoplasms, and cancer as well as diseases characterized by hyperplastic growth such as psoriasis. Combination chemoprevention is the prophylactic or preventive administration of more than one agent to delay, reverse, suppress or prevent premalignant molecular or histological lesions from progressing to invasive cancer. One example is the administration of SFN for the prevention of melanoma.

Dermatoscopy: Examination of skin lesions with a dermatoscope. This traditionally consists of a magnifier (typically ×10), a non-polarized light source, a transparent plate and a liquid medium between the instrument and the skin, and allows inspection of skin lesions unobstructed by skin surface reflections. Modern dermatoscopes dispense with the use of liquid medium and instead use polarized light to cancel out skin surface reflections. Dermatoscopy is also known as dermoscopy or epiluminescence microscopy. For example, a dermatoscope can be useful to dermatologists in determining the degree of atypia of a nevus without or prior to resorting to biopsy. Dermatoscopy can be enabled with analog and/or digital imaging (videodermatoscopy). Digital dermatoscopy images can be stored and compared to later images from the same subject or from other subjects. Common systems for digital dermoscopy are Fotofinder, Molemax or Easyscan.

Diagnostic: Identifying the presence or nature of a biological or medical condition, such as, but not limited to, presence of a genetic mutation, systemic or localized concentration in a subject of an administered pharmaceutical composition, occurrence of dysplastic nevus syndrome, or occurrence of melanoma.

Dysplastic nevus syndrome: A medical condition characterized by the presence on the skin of multiple dysplastic, unusual, or atypical nevi or moles. In some examples, the syndrome occurs in multiple family members, possibly over multiple generations, resulting in a family history of dysplastic nevus syndrome or of melanoma. In some examples, individuals may be at increased risk of melanoma versus the general population. "Dysplastic nevus syndrome" is also known as "Familial atypical multiple mole-melanoma (FAMM) syndrome" and "familial melanoma syndrome."

Enteral administration: Administration that involves absorption of a drug through the gastrointestinal tract.

Immunoassay: A biochemical test in which antibodies are used to target molecules to determine their presence in a sample from a subject. Secondary marker(s) may be used to amplify and detect the presence of primary antibody. The secondary marker may be another antibody, agent, or reaction for detecting and amplifying the resulting signal indicating the presence of the primary antibody. Examples of specific types of immunoassay include ELISA, Western blot, or RIA assay.

Isolated: An "isolated" chemical or biological component, such as a compound, nucleic acid, protein (including antibodies), or organelle, has been substantially separated or purified away from other chemical or biological components in the environment (such as an animal, a plant, or a cell) in which the component naturally occurs. Various techniques may be used for isolating, including excising, biopsying, extracting, purifying, and concentrating. In an example, SFN can be extracted from certain agricultural products (for example broccoli, brussel sprouts, cabbage, cauliflower, collard or mustard greens, kohlrabi, bok choy, rapini, turnips, rutabaga, arugula, certain radishes, and watercress). It may then be purified of contaminants and potential toxins, concentrated, and quantified as to both amount and final concentration (or any combination of these steps).

MC1R: MelanoCortin 1 Receptor, which is the receptor of alpha-melanocyte stimulating hormone. The "MC1R gene" encodes MC1R. MC1R is a major genetic determinant of UV-induced melanocyte oxidative responses, robustness to DNA damage, and melanoma risk or susceptibility. MC1R may be essential for maintenance of a normal redox state in melanocytes, and possibly more so in nevi that are under constant oxidative stress. Some mutations in the MC1R gene can result in a loss of gene or protein function and may be associated with increased risk of melanoma. As a possible genetic determinant of melanoma risk, MC1R may be used in some examples as an indicator in subject selection for SFN melanoma prevention therapy. In some examples, MC1R may be sequenced from saliva samples, and loss of function mutations may be detected. An exemplary nucleic acid sequence of a human MC1R gene is presented in GEN-BANK® Accession No. BC007856.2 as of Jul. 15, 2006, incorporated herein by reference.

Melanoma: A form of cancer that originates in melanocytes (cells that make the pigment melanin). Melanocytes are found primarily in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma, and uveal melanoma.

Features that affect prognosis are tumor thickness in millimeters (Breslow's depth), depth related to skin structures (Clark level), type of melanoma, presence of ulceration, presence of lymphatic/perineural invasion, presence of tumor infiltrating lymphocytes (if present, prognosis is better), location of lesion, presence of satellite lesions, and presence of regional or distant metastasis.

Nevi: Melanocytic nevi may be broadly categorized into normal nevocellular nevi, (or benign neoplasms of melanocytes), and atypical nevi. A neoplasm is a new growth or shape in a tissue. A distinction may be drawn between common acquired nevi, which are smaller than 3 mm, symmetrical, well-defined, and of uniform tan-brown coloration, and atypical nevi which are generally greater than 5 mm in diameter, often asymmetrical, with indistinct or irregular borders, and of variegated color, often including pink and red. "Atypical nevi" is the clinical description of the same lesions known pathologically as "dysplastic nevi." Histopathology criteria essential for diagnosis include thickness of the lesion, extent of penetration, degree of ulceration, presence of lymphocytic infiltrates.

A six-tiered scale (A-F) may be used to classify nevi based on the degree of atypical morphology observed in a nevus ("F" being the least atypical, and "A" being the most atypical). Such morphological observations may be conducted visually or photographically, with/without magnification, with/without applied contrasting agents, in vivo on the skin of a subject or in situ using a sample (e.g. biopsy) from a subject. As an example, one purpose of the present technology is to reduce the progression of nevi from less atypical ("F") toward more atypical ("A"). As a further example, a tiered scale (for example A-F) may define less to more atypical conditions as a progression with respect to one or more of the following possible nevus properties in any combination: asymmetry, distinctiveness and/or regularity of borders, variegation in color, thickness, penetration, ulceration, lymphocytic infiltration. These are just example properties, and other properties may be useful. As a further example, this progression can be associated with the occurrence of melanoma, so that reducing or slowing this progression can be associated with prevention of melanoma. For scoring and classification methods, see Wang et al., Journal of Investigative Dermatology (2008) 128: 1997-2002, which is incorporated herein in its entirety.

Pharmaceutical composition: A chemical or biological compound or mixture capable of inducing a desired prophylactic, preventive, or therapeutic effect when properly administered to a subject. Such a composition is prepared consistently with accepted pharmaceutical practice to promote safety of the subject and decrease risk of adverse reactions in the subject after administration. Generally, a pharmaceutical composition includes a pharmaceutically acceptable carrier.

In examples herein that employ pharmaceutically acceptable carriers, these are the conventional carriers. Remington's Pharmaceutical Sciences, by E. W. Martin, Mack Publishing Co., Easton, Pa., 15th Edition, 1975, describes compositions suitable in some examples for pharmaceutical delivery of the compound herein disclosed.

In general, the nature of a carrier will depend on the desired final nature of the composition and the mode of administration being employed. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to precluding the onset or inhibiting the full development of a disease such as melanoma and is a form of prophylaxis. "Treating" refers to a therapeutic intervention that ameliorates a sign or symptom of a disease or pathological condition such as melanoma after it has begun to develop. "Ameliorating" refers to the reduction in the number or severity of signs or symptoms of a disease, such as cancer.

Sample: A biopsy, serum, blood, plasma or other substance from an animal (e.g., human) that includes biomolecules and antibodies representative of those present in the animal. Samples can include processed blood samples, secretions, and the like. As an example, a sample may be tissue from a nevus harvested during a biopsy and then subjected to one or more visual inspections and/or biochemical assays.

STAT1 and STAT3: Signal Transducer and Activation of Transcription (STAT) proteins are a collection of transcription factors activated by tyrosine phosphorylation, which participate in normal cellular events. As examples, of the 7 known STAT proteins, STAT 1, 3, 5a and 5b have important roles in controlling cell-cycle progression and apoptosis. For example, STAT1 is considered a tumor suppressor gene as it inhibits growth and acts as a mediator of apoptosis. And as another example, STAT3 has been shown to contribute to oncogenesis by upregulating genes involved with apoptosis inhibition, cell cycle regulation, and induction of angiogenesis. STAT3 also participates in the regulation of tumor immune evasion by inhibiting expression of proinflammatory mediators while promoting expression of immune-suppressing factors. When the STAT proteins become dysregulated, the resultant aberrant cellular proliferation is known to contribute to carcinogenesis. Atypia in nevi correlate with the expression of STAT1 and STAT3 in melanocytic nevi of subjects with melanoma. In some examples, STAT expression may be analyzed immunohistologically in biopsy tissue, for example in biopsies of nevi. An example human STAT1 gene is presented in GENBANK® Accession No. BC002704.2 as of Jul. 15, 2006. An example human STAT3 gene is presented in GENBANK® Accession No. BC000627.2 as of Jul. 15, 2006.

Subject: Living multi-cellular vertebrate organisms, a category that includes both human and veterinary subjects, including human and non-human mammals.

Therapeutically effective amount: A quantity of a specific substance that alone, or together with a pharmaceutically acceptable carrier or one or more additional pharmaceutical agents, is sufficient to achieve a desired effect in a subject being treated. For instance, this can be the amount of SFN necessary to prevent, reduce, inhibit, or suppress growth of an atypical nevi or a tumor. When administered to a subject, a dosage will generally be used that will achieve target tissue concentrations (for example, systemically or in nevi) that have been shown to achieve a desired effect, for example reducing the progression of nevi from less to more atypical, or preventing melanoma.

Effective amounts of a pharmaceutical agent can be determined in many different ways, such as by assaying for improvement or maintenance of a physiological condition of a subject, for example a subject having dysplastic nevus syndrome. Effective amounts also can be determined through various in vitro, in vivo, or in situ assays.

Therapeutic agents can be administered in a single dose, or in several doses, for example thrice daily, twice daily, daily, bi-weekly, weekly, monthly, or bi-monthly, during a course of treatment. However, the effective amount can be dependent on the source of the pharmaceutical composition, the subject being treated, the severity and type of the condition being treated, and the manner of administration.

Unless explained otherwise, all technical and scientific terms used herein have the same meaning as commonly understood to one of ordinary skill in the art to which this disclosure belongs. In case of conflict, the present specification, including explanations of terms, will control. Explanation of common terms and methods in pharmacology may be found in Remington's Pharmaceutical Sciences, by E. W. Martin, Mack Publishing Co., Easton, Pa., 15th Edition, 1975 and Goodman & Gilman's The Pharmacological Basis of Therapeutics, by L. Brunton et al., The McGraw Hill Companies, Inc., Twelfth Edition (2011).

All publications, patent applications, patents, and other references mentioned herein are incorporated by reference in their entirety for all purposes.

Although methods and materials similar or equivalent to those described herein can be used to practice or test the disclosed technology, suitable methods and materials are described below. The materials, methods, and examples are illustrative only and not intended to be limiting.

The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Although methods and materials similar or equivalent to those described herein can be used in the practice or testing of the present disclosure, suitable methods and materials are described below. All publications, patent applications, patents, GENBANK® Accession numbers and other references mentioned herein are incorporated by reference in their entirety. In case of conflict, the present specification, including explanations of terms, will control. In addition, the materials, methods, and examples are illustrative only and not intended to be limiting.

SFN and Pharmaceutical Compositions

The chemical structure of Sulforaphane (SFN) is provided below, and Table 1 follows, listing example analogues of SFN.

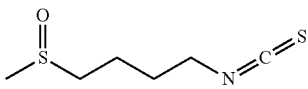

TABLE 1

Chemical formula of example SFN analogues

| Chemical name | Common name | Chemical formula |
|---|---|---|
| 3-(Methylthio)-propyl isothiocyanate | Iberverin | $CH_3$—S—$(CH_2)_3$—N=C=S |
| 4-(Methylthio)-butyl isothiocyanate | Erucin | $CH_3$—S—$(CH_2)_4$—N=C=S |
| 5-(Methylthio)-pentyl isothiocyanate | Berteroin | $CH_3$—S—$(CH_2)_5$—N=C=S |
| 3-(Methylsulfinyl)-propyl isothiocyanate | Iberin | $CH_3$—SO—$(CH_2)_3$—N=C=S |
| 4-(Methylsulfinyl)-butyl isothiocyanate | Sulforaphane | $CH_3$—SO—$(CH_2)_4$—N=C=S |
| 5-(Methylsulfinyl)-pentyl isothiocyanate | Alyssin | $CH_3$—SO—$(CH_2)_5$—N=C=S |
| 3-(Methylsulfonyl)-propyl isothiocyanate | Chelrolin | $CH_3$—$SO_2$—$(CH_2)_3$—N=C=S |
| 4-(Methylsulfonyl)-butyl isothiocyanate | Erysolin | $CH_3$—$SO_2$—$(CH_2)_4$—N=C=S |
| 5-(Methylsulfonyl)-pentyl isothiocyanate | Alyssin sulfone | $CH_3$—$SO_2$—$(CH_2)_5$—N=C=S |

SFN is found in cruciferous vegetables such as cabbage, broccoli, broccoli sprouts, brussel sprouts, cauliflower, cauliflower sprouts, bok choy, kale, collards, arugula, kohlrabi, mustard, turnip, red radish and watercress. In the plant, it is present in bound form as glucoraphanin, a glucosinolate. D,L-Sulforaphane is a synthetic analogue of broccoli-derived L-isomer. Sulforaphane is often formed from glucoraphanin on plant cell damage via an enzymatic reaction. Various synthetic methods of producing sulforaphane are known in the art. Sulforaphane was synthesized as early as 1948 by Schimd and Karrer (Schimd H. and Karrer, P.; Helvetica Chimica Acta. 1948; 31; 6: 1497-1505). Stabilized forms of sulforaphane have also been produced, see U.S. Published Patent Application No. 2008/0176942, Jul. 24, 2008, incorporated herein by reference.

Additional methods are known (see U.S. Pat. No. 5,882, 646 and U.S. Published Patent Application No. 2009/ 0247477). An exemplary non-limiting method for producing sulforaphane includes extracting three-day-old broccoli sprouts with hot water, treating with myrosinase and freeze drying the treated extract under pharmaceutically appropriate manufacturing conditions, see Cornblatt et al., *Carcinogenesis* (2007) 28: 1485-1490, which is incorporated herein in its entirety. Variations on any of these methods are known to or will be readily apparent to those skilled in the art. It is not intended that this disclosure be limited to any particular process of manufacture or mode of production.

Generally, the methods disclosed use compositions that are formulated for pharmaceutical use. The methods do not include simple ingestion of a cruciferous vegetable such as broccoli, but rather include the use of a pharmaceutical composition comprising sulforaphane in an isolated or synthetic form. Pharmaceutically acceptable carriers include, but are not limited to, physiological saline, Ringer's, phosphate solution or buffer, buffered saline, and other carriers known in the art.

The route of administration may be one or more of buccal (via membranes of the mouth), oral, or enteral (via the gastrointestinal tract). The pharmaceutically acceptable carrier can also be selected on the basis of the desired route of administration of SFN. The desired route of administration may be one or more of buccal, oral, or enteral. For example, in a one embodiment the carrier is suitable for oral administration. In some embodiments, the composition includes a carrier or additional agent that is suitable for promoting delivery of the compound(s) to the gastrointestinal or intestinal tract.

Pharmaceutical compositions intended for oral administration may be prepared according to any method known in the art for the production of pharmaceutical compositions, and such compositions may contain one or more agents selected from the group consisting of sweetening agents, flavoring agents, coloring agents, and preserving agents in order to provide pharmaceutically suitable and palatable preparations.

In an embodiment, methods include administering a pharmaceutical composition that includes about 50 to about 400

µM of SFN. For example, the methods include administering a pharmaceutical composition that includes about 50, about 100, or about 200 µM of SFN. In a further embodiment, the methods include administering a pharmaceutical composition that includes about 0.5 to about 10 µM of SFN per kilogram of bodyweight of a subject. For example, the methods include administering a pharmaceutical composition that includes about 0.5, about 2.0, or about 4.0 µM of SFN per kilogram of bodyweight of a subject.

Oral delivery of the pharmaceutical compositions of the present disclosure can include compositions, as are well known in the art, to provide prolonged or sustained delivery of the drug to the gastrointestinal and/or intestinal tract by any number of mechanisms. These include, but are not limited to, pH sensitive release from the dosage form based on the changing pH of the small intestine, slow erosion of a tablet or capsule, retention in the stomach based on the physical properties of the composition, bioadhesion of the dosage form to the mucosal lining of the intestinal tract, or enzymatic release of the active drug from the dosage form. For some of the therapeutic compositions, the intended effect is to extend the time period over which the active drug molecule is delivered to the site of action by manipulation of the dosage form. Thus, enteric-coated controlled release compositions are within the scope of the present disclosure. Suitable enteric coatings include cellulose acetate phthalate, polyvinylacetate phthalate, hydroxypropylmethylcellulose phthalate and anionic polymers of methacrylic acid, and methacrylic acid methyl ester.

The SFN that is useful in the present methods is of a quality and stability suitable for pharmaceutical use. Oral administration includes buccal or "sub-lingual" administration via membranes of the mouth. This can be accomplished using lozenges or a chewable gum containing SFN. The SFN can be deposited in a flavored base, usually sucrose, acacia, or tragacanth, and pastilles comprising the SFN in an inert base such as gelatin and glycerin or sucrose and acacia.

Multiple forms of SFN are appropriate for oral administration. In different embodiments, these include but are not limited to stock SFN provided as a solid (including powders) or a liquid. Stock SFN may then be further mixed and prepared for administration.

Solid dosage forms for oral administration include, but are not limited to, capsules, tablets, pills, powders, and granules. In such solid dosage forms, the active compounds are mixed with at least one pharmaceutically acceptable excipient or carrier such as, but not limited to, sodium citrate or dicalcium phosphate.

The pharmaceutical composition can include fillers or extenders, such as starches, lactose, sucrose, glucose, mannitol, and silicic acid. Optionally, binders such as, for example, carboxymethylcellulose, alginates, gelatin, polyvinylpyrrolidone, sucrose, and *acacia* can be include. In additional embodiments, the pharmaceutical compositions include humectants, such as glycerol, and/or disintegrating agents, such as agar-agar, calcium carbonate, potato or tapioca starch, alginic acid, certain silicates, and sodium carbonate. The compositions can also include solution retarding agents such as paraffin, absorption accelerators such as quaternary ammonium compounds, wetting agents such as acetyl alcohol and glycerol mono stearate, absorbents such as kaolin and bentonite clay, and/or lubricants such as talc, calcium stearate, magnesium stearate, solid polyethylene glycols, sodium lauryl sulfate.

In the case of capsules, tablets and pills, the dosage form can also comprise buffering agents. Tablets may contain the active ingredient in admixture with non-toxic pharmaceutically acceptable excipients, which are suitable for the production of tablets. These excipients may be, for example, inert diluents, such as calcium carbonate, sodium carbonate, lactose, calcium phosphate or sodium phosphate, granulating and disintegrating agents, for example, maize starch, or alginic acid, binding agents, for example starch, gelatin or acacia, and lubricating agents, for example magnesium stearate, stearic acid, or talc.

The tablets may be uncoated, or they may be coated by known techniques to delay disintegration and adsorption in the gastrointestinal tract and thereby provide a sustained action over a longer period. For example, a time delay material such as glyceryl monostearate or glyceryl distearate may be employed.

Pharmaceutical compositions suitable for oral administration can be presented in discrete units each containing a predetermined amount of at least one therapeutic compound useful in the present methods; as a powder or granules; as a solution or a suspension in an aqueous or non-aqueous liquid; or as an oil-in-water or water-in-oil emulsion. As indicated, such compositions can be prepared by any suitable method of pharmacy, which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product.

For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made by molding, in a suitable machine, the powdered compound moistened with an inert liquid diluent.

Solid compositions of a similar type can also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) in a certain part of the intestinal tract, optionally, in a delayed manner. Examples of embedding compositions which can be used include polymeric substances and waxes. The active compounds can also be in micro-encapsulated form, if appropriate, with one or more of the above mentioned excipients.

Liquid dosage forms for oral administration include, but are not limited to, pharmaceutically acceptable emulsions, solutions, suspensions, syrups, teas, and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In some embodiments, suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

A drinkable tea containing SFN can also be used in the present methods. A drinkable tea may be taken in a liquid form or in a once pulverized or granulated form together with water or hot water. When it is in a powdery or granular form, the drinkable tea may be contained in a cavity of mouth before taking hot water or water like the conventional powdery or granular drinkable tea, or it may be taken after once dissolving in hot water or water. One or more components, such as a sugar, mint, or other flavor, can be added to improve taste and easiness as a drinkable drug. Teas, syrups and elixirs can be formulated with sweetening agents, for example glycerol, sorbitol or sucrose. Such compositions can also contain a demulcent, a preservative, and flavoring and coloring agents.

SFN can be administered in conjugation with radiation therapy and/or another agent such as interferon (including high-dose interferon), dacarbazine, IL-2 or other cytokine, BCG vaccine, imiquimod, ipilimumab, vemurafenib and temozolomide. In particular, the pharmaceutical compositions of the present disclosure, or compositions in which they are included, can be administered orally, for example, as tablets, coated tablets, dragees, troches, lozenges, aqueous or oily suspensions, dispersible powders or granules, emulsions, hard or soft capsules, or syrups, teas, or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Compositions for oral use may also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin, any of a variety of herbal extracts, milk, olive oil, or other plant oil.

Aqueous suspensions can be produced that contain the active materials in admixture with excipients suitable for the production of aqueous suspensions. Such excipients are suspending agents, for example, sodium carboxymethylcellulose, methylcellulose, hydroxypropylmethylcellulose, sodium alginate, polyvinylpyrrolidone gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate.

The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the active ingredients in an omega-3 fatty acid, a vegetable or plant oil, for example arachis oil, olive oil, sesame oil, broccoli oil, or coconut oil, or in a mineral oil such as liquid paraffin. The oily suspensions may contain a thickening agent, for example beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

The present disclosure may also include safe and effective amounts of isotonicity agents, e.g., salts, such as sodium chloride, or non-electrolyte isotonicity agents such as sorbitol, and mannitol.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103), cyclodextrin, or other agents known to those skilled in the art. Typically, such co-solvents are employed at a level of from 0.01% to 2% by weight.

Pharmaceutically acceptable excipients and carriers encompass all the foregoing and the like. The above considerations concerning effective compositions and administration procedures are well known in the art and are described in standard textbooks. See e.g. Gennaro, A. R., *Remington: The Science and Practice of Pharmacy*, 15th Edition, (Lippincott, Williams and Wilkins), 2000; Hoover, John E., *Remington's Pharmaceutical Sciences*, Mack Publishing Co., Easton, Pa., 1975; Liberman et al., Eds., *Pharmaceutical Dosage Forms*, Marcel Decker, New York, N.Y., 1980; and Kibbe et al., Eds., *Handbook of Pharmaceutical Excipients* (3rd Ed.), American Pharmaceutical Association, Washington, 1999.

Methods for Reducing the Progression of Atypical Nevi and Preventing Melanoma

Methods are provided for preventing melanoma in a subject. The methods include selecting a subject at risk of developing melanoma, and administering orally to the subject a therapeutically effective amount of a pharmaceutical composition comprising an effective amount of SFN, thereby preventing melanoma from developing in the subject. Thus, in several embodiments, the methods can prevent the appearance of melanoma precursor lesions and the appearance of superficial spreading melanoma, nodular melanoma, acral lentiginous melanoma, lentigo maligna melanoma, and other melanomas.

In some non-limiting examples, the methods reduce the number of new atypical nevi appearing and/or of reduce the progression of nevi from a less to a more atypical type. Thus, reducing progression includes, but is not limited to, reducing emergence of additional nevi and/or reducing the conversion of atypical nevi to more atypical types.

In some embodiments, subjects are selected because they are at increased risk of developing melanoma. Increased risk for melanoma can be defined in comparison to the general population as a history of atypical nevi, a history of dysplastic nevi syndrome, a history of melanoma, a genotype including a loss of function mutation in an MC1R gene, and/or other indicators of increased risk of melanoma. In some embodiments, subjects are selected that have a loss of function mutation in an MC1R gene and/or an immediate or extended, living or deceased family member having this mutation. See US Patent Application Publication No. 2011/0201011, which is hereby incorporated by reference in its entirety, for methods of selecting for a subject with a loss of function mutation in an MC1R gene. In other embodiments, a subject is selected that has a relatively high number of atypical nevi and/or a high degree of atypia among these nevi. In another embodiment, a subject can be selected that has a history of UV exposure to the skin. Any of these can be a condition for selecting subjects with increased risk of developing melanoma.

Risk factors for melanoma can be ascertained through clinical interviews, and/or through clinical testing, and/or through subjects reporting via questionnaires, and/or through epidemiological data indicating an at-risk population, and/or any other means. Clinical interviews and questionnaires can be conducted in accordance with accepted clinical practice known to those in the medical field. Clinical testing can be conducted in accordance with accepted clinical practice known to those in the medical field and can include genetic testing for loss of function mutations in MC1R genes. MC1R testing can involve genotyping from harvested saliva samples of living subjects or their relatives.

The presence of melanoma and the number and degree of atypia of nevi may be determined by any of various visual means, including but not limited to visual inspection, such as with the naked eye, with the aid of an optical device such as a dermatoscope, inspection of analog or digital photographs or video of a subject's skin, or the application of other techniques known in the field of dermatoscopy. Visual inspection can be enhanced by the use of dyes and contrast agents. The presence and type of melanoma or a nevi can also be assessed using biopsies and histological methods known in the medical field. Any of these techniques may be applied at selected locations on the body, and/or they may be part of a whole body screening. The presence of nevi reaching 4 or more millimeters in diameter can indicate increased risk of melanoma compared with smaller nevi. In some embodiments, smaller nevi may be a risk indicator. The presence of one or more, or, in some embodiments, two or more nevi reaching 4 or more millimeters in diameter can indicate increased risk of melanoma compared with smaller nevi. The presence of two or more nevi, with one or more of those nevi having been classified as atypical on a tiered scale, can indicate increased risk of melanoma compared with a lack of atypical nevi. Thus, fewer subjects can be selected for treatment using the methods disclosed here.

In some embodiments, the degree of atypia can be assessed morphologically and/or visually and/or photographically on a tiered scale, with successive tiers used to classify lesser and greater degrees of atypia. In an embodiment, clinical assessment of atypia may be mild, moderate, and severely atypical. In another embodiment, a tiered scale may have tiers, for example, labeled "A" through "F," with "F" indicating a least atypical nevus, and with "A" indicating a most atypical nevus. In an embodiment nevi are classified based on observed properties of a nevi, including size, shape/asymmetry/roundness/presence or projections, continuity/smoothness/irregularity of border, color/pigmentation/variegation, degree raised above skin surface, firmness, continuity vs. broken surface structure, the presence of other structural features or abnormalities, and known evolution over time. In an embodiment, histopathological assessment of atypia may be mild, moderate, and severe dysplasia (atypia).

The methods include administering a therapeutically effective amount of a pharmaceutical composition including SFN to the subject, wherein the pharmaceutical composition is administered orally. Any of the pharmaceutical compositions disclosed herein can be used in these methods. In specific non-limiting examples, the pharmaceutical composition is a tea or a gel capsule.

In an embodiment, methods include administering a pharmaceutical composition that includes about 50 to about 400 µM of SFN. For example, the methods include administering a pharmaceutical composition that includes about 50, about 100, or about 200 µM of SFN. In a further embodiment, the methods include administering a pharmaceutical composition that includes about 0.5 to about 10 µM of SFN per kilogram of bodyweight of a subject. For example, the methods include administering a pharmaceutical composition that includes about 0.5, about 2.0, or about 4.0 µM of SFN per kilogram of bodyweight of a subject.

The pharmaceutical composition can be administered at selected time intervals over a treatment course of selected duration. The pharmaceutical composition can be administered thrice daily, twice daily, daily, bi-weekly, weekly or monthly. The subject can be treated over an extended period, such as for weeks, months or years. Specific examples include, but are not limited to, administration for a week, about ten days, about two weeks, about a month, about three months, about six months, about nine months, about a year, about two years, about three years, about five years, about ten years, or for the remaining lifespan of the subject.

In some embodiments, the effectiveness of the administration of SFN can be monitored by testing for the expression of STAT1 and/or STAT3 in a biological sample obtained from the subject. In an embodiment, testing for the expression of STAT1 or STAT3 in biopsy samples is accomplished using an immunoassay or an immunohistological assay, for example using antibodies to either or both of STAT1 and STAT3, where antibodies to both are known in the field and commercially available. In an embodiment, the sample in which STAT expression is monitored is tissue from a biopsy, for example a biopsy of normal skin or a biopsy of a nevus.

In one embodiment, nucleic acid based methods are utilized. These methods include serial analysis of gene expression (SAGE techniques), RT-PCR, quantitative PCR, real time PCR, Northern blot, dot blots, microarrays, amongst others. Generally, with regard to nucleic acids, any method can be utilized provided it can detect the expression of target gene mRNA (STAT1 and/or STAT3) as compared to a control. In other embodiments, the amount of STAT1 and/or STAT3 polypeptides is measured. This can be accomplished using immunoassays or using spectrometric methods. Both monoclonal and polyclonal antibodies, and fragments thereof, can also be utilized to detect and quantify the expression of STAT1 and STAT3. This can be accomplished, for example, by immunohistochemistry, immunoassay (such as enzyme-linked immunosorbent assay (ELISA) or radioimmunoassay (RIA)), Western blotting, flow cytometric or fluorimetric detection. The antibodies (or fragments thereof) can be employed histologically, as in immunofluorescence or immunoelectron microscopy, for in situ detection of STAT1 and/or STAT3. In situ detection includes contacting a histological specimen from a subject with labeled antibody, and detecting binding of the antibody to monocytes within the sample. A wide variety of histological methods (such as staining procedures) can be modified in order to achieve such in situ detection.

One of skill in the art can readily identify an appropriate control, such as a sample from a subject known not to have a melanoma or atypical nevi (a negative control), a sample from a subject known to have melanoma (a positive control), or a known amount of nucleic acid encoding STAT1 and/or STAT3 (a standard or a normal level found in a healthy subject).

The following examples are provided to illustrate certain particular features and/or embodiments. These examples should not be construed to limit the disclosure to the particular features or embodiments described.

EXAMPLES

Example 1

SFN's Effect on Melanoma Cells In Vitro

This example illustrates that sulforaphane (SFN) modulates growth of cells (SK-MEL31 and SK-MEL37), Cyclin B1, Cdk1, and Cdc25.

It was demonstrated that SFN inhibits melanoma cell growth in vitro. FIG. 1 shows the effect of SFN on SK-MEL31 and SK-MEL37 cell viability as determined through a trypan blue dye exclusion assay. 4,000 cells were plated in 6-well plates, allowed to attach overnight, and exposed to different concentrations of SFN for 24, 48, or 72 h at 37° C. A stock solution of SFN was prepared in DMSO, and an equal volume of DMSO was added to the controls. Data are mean+/−standard error (SE) of 3 determinations. Similar results were observed in replicate experiments.

Figure 2:
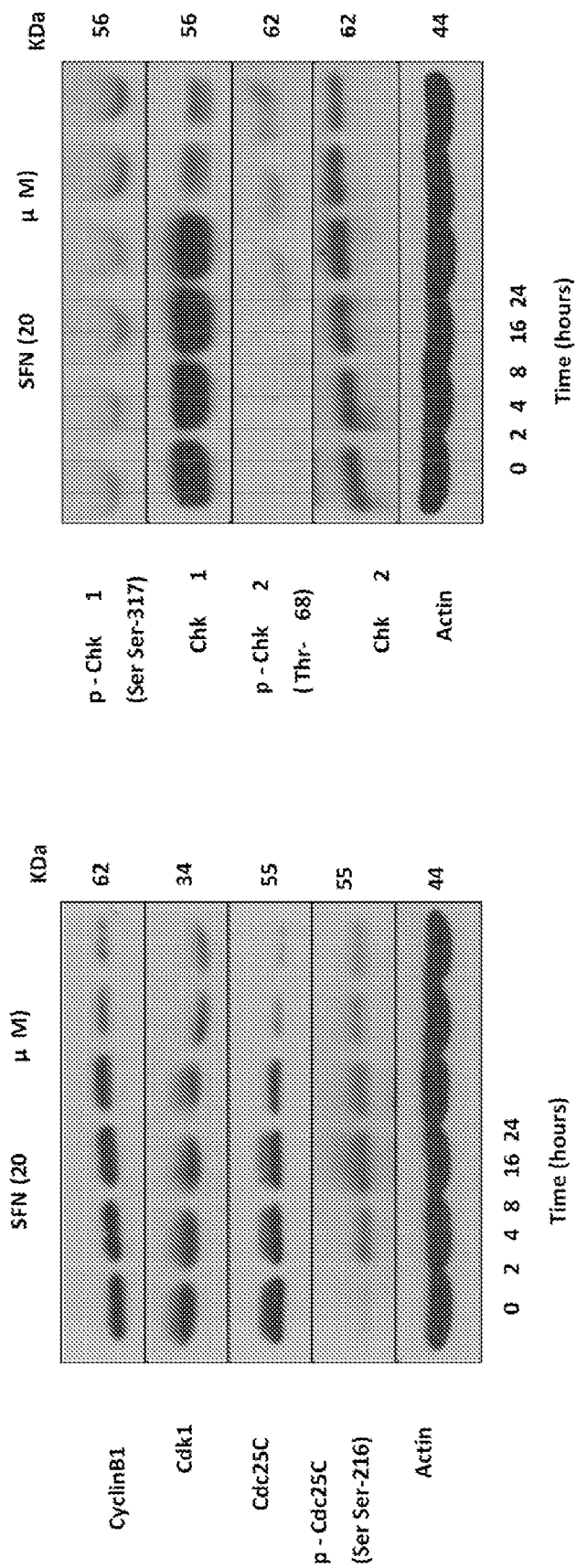
FIG. 2 is a set of digital images demonstrating that SFN inhibits melanoma cell Cyclin B1, Cdk1, and Cdc25 in vitro.

It was also demonstrated that SFN inhibits melanoma cell Cyclin B1, Cdk1, and Cdc25 in vitro. FIG. 2 shows immunoblotting for cyclinB1, Cdk1, Cdc25C and Ser-216 phosphorylated Cdc25C using lysates from SK-MEL31 cells treated with 20 µM SFN for the indicated time periods. FIG. 2 also shows immunoblotting for p-Chk1 (Ser-317 phosphorylated Chk1), total Chk1, p-Chk2 (Thr-68 phosphorylated Chk2) and total Chk2 using lysates from SK-MEL31 cells treated with 20 µM SFN for the indicated time periods. The blots were stripped and re-probed with anti-actin antibody to normalize for differences in protein loading.

Example 2

SFN's Effect on Hu Melanoma Xenotransplants

Figure 3:
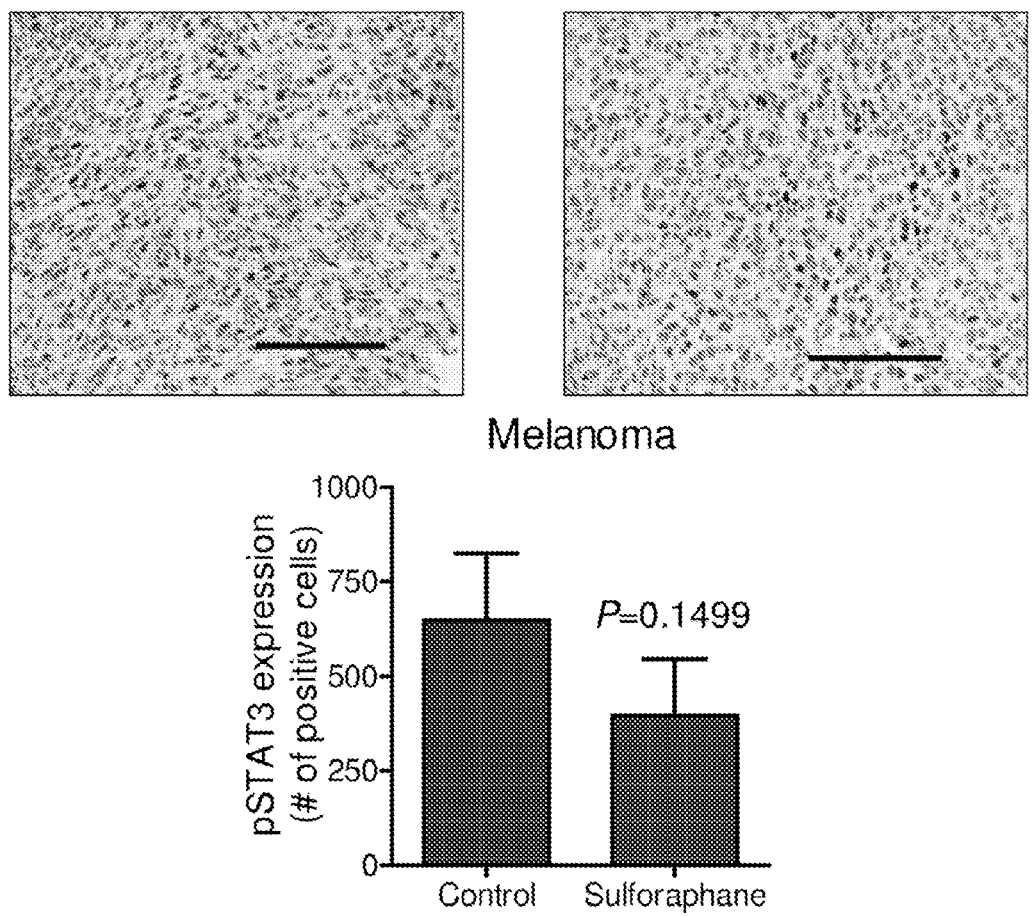
FIG. 3 is a set of digital images and a bar graph demonstrating that oral SFN modulates STAT3 in human to mice melanoma xenotransplants.

As shown in FIG. 3, D,L-SFN administered orally to SCID mice lowered STAT3 expression in human melanoma cells transplanted into the mice.

Example 3

SFN Induces Apoptosis in Human Melanoma Cells SK-MEL 31 and Retards Growth of SK-MEL 31 Xenografts In Vivo This example provides materials and methods for Examples 4-10. Examples 4-10 illustrate that SN increased apoptosis of human melanoma cells. SFN inhibited proliferation of cultured SK-MEL 31 cells by inducing apoptosis characterized by appearance of cells with sub-G0/G1 DNA content, cleavage of poly (ADP-ribose) polymerase (PARP), formation of cytoplasmic histone associated DNA fragments, and condensed nucleus. Oral administration of SFN significantly retarded the growth of SK-MEL 31 xenografts in nude mice, accompanied by increase of apoptotic bodies in SFN treated tumor specimen by TUNEL assay. SFN induced apoptosis was associated with down regulation of Bcl-XL, XIAP and cIAP1, release of cytochrome-c and Smac/DIABLO into the cytoplasm and activation of caspas-8, -9 and -3. Introduction of general and specific caspase inhibitors blocked the activation of caspase-3 and subsequent apoptosis after SFN exposure. These data show the pro-apoptotic effect of SFN against human melanoma both in vitro and in vivo.

D,L-SFN (>99% pure) was purchased from LKT Laboratories (St Paul, Minn.), and dissolved in DMSO before use. RPMI 1640, penicillin/streptomycin antibiotic mixture, and fetal bovine serum were from Gibco (Grand Island, N.Y.), propidium iodide and 4',6'-diamidino-2-phenylindole-dihydrochloride (DAPI) were from Sigma (St Louis, Mo.). LIPO-FECTAMINE 2000™ and G418 were purchased from Invitrogen (Carlsbad, Calif.). RNaseA was purchased from Promega (Madison, Wis.), and the reagents for electrophoresis were from Bio-Rad (Hercules, Calif.). Antibodies for Bcl-XL, Bak and cytochrome c were purchased from Santa Cruz Biotechnology (Santa Cruz, Calif.), antibodies specific for Bax, Smac/DIABLO, cleaved caspase-3 and cleaved caspase-8, cleaved caspase-9, cIAP1 and poly (ADP-ribose) polymerase (PARP) were purchased from Cell Signaling Technology (Beverly, Mass.), anti Bcl-2 antibody was purchased from Dakocytomation (Denmark), anti XIAP (X-linked inhibitor of apoptosis) antibody was purchased from BD PharMingen (San Diego, Calif.). Anti actin antibody was purchased from Oncogene Research Products (Boston, Mass.). The caspase inhibitors z-VAD fmk (general caspase inhibitor), z-IETD fmk (caspase-8 specific inhibitor) and z-LEHD fmk (caspase-9 specific inhibitor) were purchased from MP Biochemicals (Aurora, Ohio). The caspase-8 and caspase-9 colorimetric assay kits were purchased from R&D systems (Minneapolis, Minn.). Cytoplasmic histone associated DNA fragments detection ELISA kit was purchased from Roche Diagnostics GmbH (Mannheim, Germany). ProteoExtract™ Subcellular Proteome Extraction kit was purchased from Calbiochem (San Diego, Calif.).

Cell Culture and Cell Proliferation Assays

Monolayer cultures of SK-MEL 31 cells were maintained at 37° C. in RPMI 1640 supplemented with 10% (v/v) heat inactivated fetal bovine serum and antibiotics in a humidified atmosphere of 5% CO2 and 95% air. Trypan blue dye exclusion assay was used to study the effect of SFN on proliferation of SK-MEL 31 cells. SK-MEL 31 cells were seeded in 12 well plates in triplicate at $1\times10^4$/well and allow to attach overnight. Cells were then incubated with Sulforaphane (0, 10, 20, 40 µM) for 24, 48 and 72 hours. Both floating and adherent cells were pelleted by centrifugation, and resuspended with 0.4% Trypan blue, stained and unstained cells were counted for each sample. To evaluate the effect of SFN treatment on cell cycle progression, SK-MEL 31 cells ($5\times10^5$ cells) were seeded in triplicate in T25 flasks, and allowed to attach overnight. The media was replaced with fresh complete media containing 20 µM SFN or equal volume of DMSO as control. After 24 hours of incubation, floating and attached cells were collected, washed with PBS and fixed with 70% ethanol. Fixed cells were then incubated with 80 mg/ml RNase A and 50 mg/ml propidium iodide for 30 minutes, and DNA content for cell cycle analysis quantified was analyzed using a Coulter Epics XL Flow Cytometer.

Transfection of SK-MEL 31 Cells with pSFFV-Bcl-XL Plasmid DNA

To establish Bcl-XL over-expression cells, SK-MEL 31 cells were transfected with pSFFV-Bcl-XL or pSFFV-neo plasmids at 1:2 ration (µg plasmid DNA: µl Lipofectamine) using LIPOFECTAMINE 2000™. Transiently transfected cells were selected and maintained in RPMI 1640 containing 300 μg/ml of G418 until experimentation.

Determination of Apoptosis

Apoptosis induction in SFN-treated SK-MEL 31 cells was assessed by (i) quantification of cytoplasmic histone associated DNA fragments, (ii) Western blot analysis for PARP cleavage and (iii) DAPI dye for nuclear morphology assay. For quantification of cytoplasmic histone-associated DNA fraction, SK-MEL 31 cells were seeded at $4\times10^3$ cells/well in 96-well plate and allowed to attach overnight. The media was replaced with fresh complete media containing 0, 2.5, 5, 10 μM of SFN. After 24 hours, the floating and attached cells were pelleted and lysed with lysis buffer supplied with the cell death detection ELISA kit, lysates were assayed for apoptosis according to the manual. SK-MEL 31 cells were seeded at $1\times10^4$ cells/well on a round glass coverslip in 12 well plates. Cells were then incubated for 24 hours with 0, 10, or 20 μM SFN, attached cells were fixed with 3% paraformaldehyde in PBS, permeabilized with 1% TRITON® X-100, stained with DAPI dye and inspected under a fluorescent microscope after stained with DAPI.

Western Blot Analysis $2\times10^6$ SK-MEL 31 cells were seeded into T75 flasks, after treatment with 20 μM SFN or equal volume of DMSO (control) for specified time interval; floating and attached cells were collected and lysed with TRITON® X-100/SDS lysis buffer at 4° C. for 30 minutes. Cell lysate was cleared by centrifugation at 16000 rpm for 15 min. Lysate proteins were resolved by SDS-PAGE gel electrophoresis and transferred onto nitrocellulose membrane. The membrane was immersed into a phosphate buffered saline (PBS) solution containing 0.2% TWEEN® 20 and 5% (w/v) non-fat dry milk, and then incubated with desired primary antibody for 1 hour at room temperature. After incubation with appropriate secondary antibody, the immunoreactive bands were visualized using enhanced chemiluminescence method. The conjugated horseradish peroxidase (HRP) secondary antibody was deactivated with sodium azide, then membranes were re-probed with anti-actin antibody to standardize protein loading. For cytochrome c and Smac/DIABLO, the cytosolic fractions were prepared with the PROTEOEXTRACT™ Subcellular Proteome Extraction kit according to the manufacturer's instructions and Western blot analysis were performed as described above.

Xenograft Assay

Female athymic mice (6-week-old) were purchased from Taconic (Germantown, N.Y.). SK-MEL 31 cells were suspended in pharmacological grade normal saline, and 0.1 ml suspension containing $5\times10^6$ cells was injected subcutaneously on right flank of each mouse. Mice were randomized into two groups of 10 mice per group. Experimental animals were gavaged with SFN (5.6 μmol SFN in 0.1 ml normal saline) three times per week (Monday, Wednesday and Friday) beginning two weeks before tumor implantation. Control mice received an equal volume of the vehicle. Tumor volume was determined based on measurement of the length and width of the tumor, V=½×length×width. Statistical significance of difference in tumor volume was assessed by Student's t-test. Upon the termination of the experiment, the tumor tissues were harvested and processed for analysis of apoptotic bodies by immunohistochemistry method. Tumor tissues were embedded in paraffin, sectioned (6 μm), deparaffinized and processed for determination of apoptotic bodies using APOTAG® Plus Peroxidase In Situ Apoptosis detection kit (Intergen, NY) according to the manufacturer's instructions. Brown color apoptotic bodies in tumor sections of control and SFN-treated group were counted by two pathologists independently and blindly under a microscope at 400× magnification. Four randomly selected fields on each tumor section were counted for apoptotic bodies.

Example 4

SFN Inhibits Proliferation of SK-MEL 31 Cells in Culture

The effect of SFN on proliferation of SK-MEL 31 cells was determined by trypan blue dye exclusion assays and flow cytometric analysis of cellular DNA content. All the assays were carried out in two independent experiments, and the results from a representative experiment are shown in FIG. 4. SFN treatment caused a statistically significant decrease in number of viable cells in trypan blue dye exclusion assay, $p<0.05$ (FIG. 4A). At a 24 hour time point, the number of viable cells exposed to 10, 20 and 40 μM SFN was reduced to 58%, 46% and 26% compared with control, respectively. Even greater effects appeared following 48 or 72 hours exposure to SFN at all the concentrations. The number of viable cells exposed to 10, 20 and 40 μM SFN was reduced to 27%, 23% and 10% compared to control at 48 hour time point, and to 19%, 13% and 10% at 72 hour time point ($p<0.05$). The cell cycle distribution after SFN exposure showed significantly increase of Sub-$G_0/G_1$ and $G_2M$ phase and decreased $G_0/G_1$ phase cell number ($p<0.05$), suggesting both apoptosis and cell cycle arrest at $G_2M$ phase (FIG. 4B).

Example 5

SFN Induces Apoptosis in SK-MEL 31 Cells

Figure 5A:
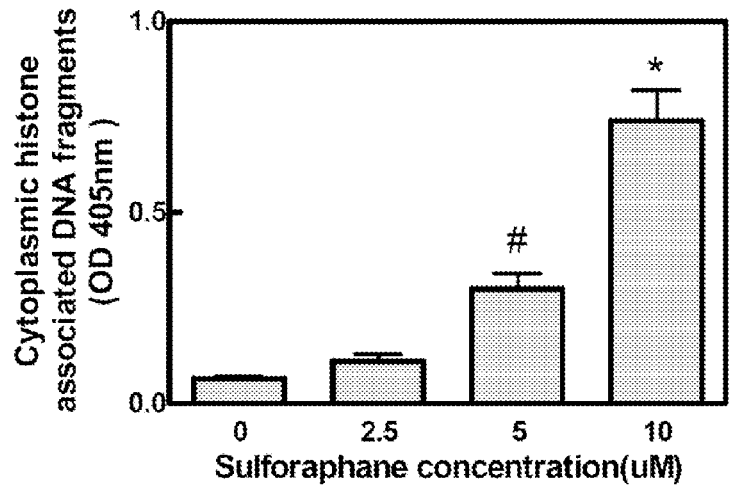
FIGS. 5A-5C are a set of bar graphs (A and C) and a digital image (B) demonstrating the effect of SFN treatment on apoptosis induction. (A) Quantification of cytoplasmic histone associated DNA fragments following a 24 h exposure to DMSO (control) or SFN (2.5, 5 or 10 µM), data are mean±SE of three determinations from a representative experiment. (B) Western blot analysis for cleaved PARP (89 kDa) using lysates from SK-MEL 31 cells exposed to 20 mM SFN after different time intervals (each lane loaded with 60 µg of lysate protein). (C) Condensed nucleus is the typical morphology change of apoptosis, the condensed nucleus ratio increased significantly after SFN treatment. The notation (#) indicates a significantly different compared with control, $p<0.05$; and the notation (*) indicates a significantly different compared with control, $p<0.01$. All experiments were repeated twice and the results were comparable.
Figure 5B:
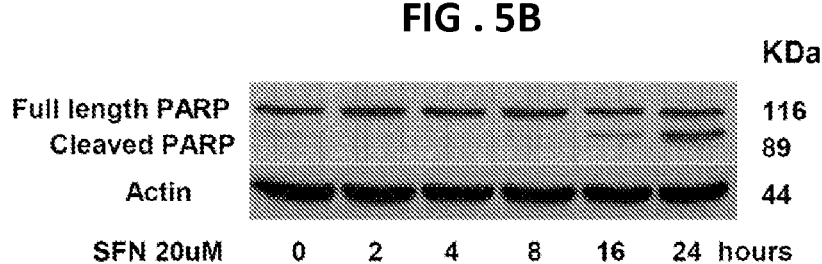
Figure 5C:
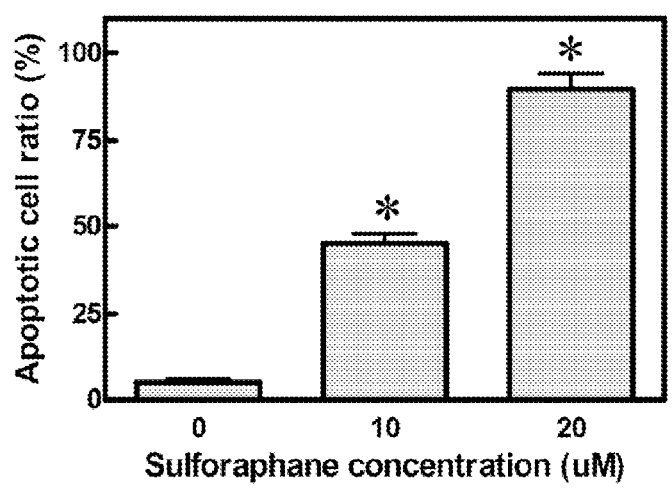

The FACS assay suggested there was apoptosis following SFN exposure in SK-MEL 31 cells, so further experiments were carried out to verify this effect. Apoptosis occurs with a number of morphological and cellular changes, such as membrane blebbing, chromatin condensation, DNA fragmentation, and key cellular proteins like PARP cleavage. Pro-apoptotic effect of SFN was assessed by ELISA based quantification of cytoplasmic histone associated DNA fragments. Incubation with SFN for 24 hours resulted in a dose-dependent and statistically significant increase in cytoplasmic histone associated DNA fragments. Exposure to 5 and 10 μM SFN resulted in ~4.7- and ~11.4-fold increase in the levels of cytoplasmic histone associated DNA fragments compared with DMSO treated control ($p<0.01$, FIG. 5A). Western blot assay showed there was an obvious increase of PARP cleavage from 16 to 24 hour after SFN treatment (FIG. 5B). DAPI dye assay was used to detect condensed nuclear, the characteristic morphology change of apoptosis. (FIG. 5C).

Example 6

Orally Administered SFN Retards Growth of SK-MEL 31 Xenografts In Vivo

Figure 6A:
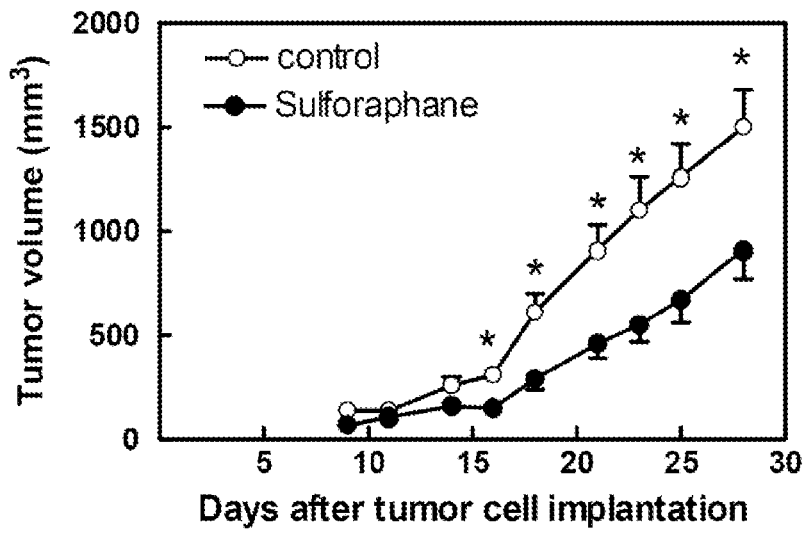
FIGS. 6A-6C are a plot (A) and a set of bar graphs (B and C) demonstrating the effect of oral administration of SFN on growth of SK-MEL 31 tumor xenografts in female nude mice. The results achieved with regard to (A) tumor volume, (B) tumor wet weight, and (C) apoptotic bodies by TUNEL assay are shown. Administration of SFN decreased the tumor burden accompanied by induced apoptosis. Data are presented as mean±SE. The notation (*) indicates a significantly different compared with control, $p<0.01$ by Student's t-test, while the notation (#) indicates a significantly different result compared with control, $p<0.05$ by Student's t-test.
Figure 6B:
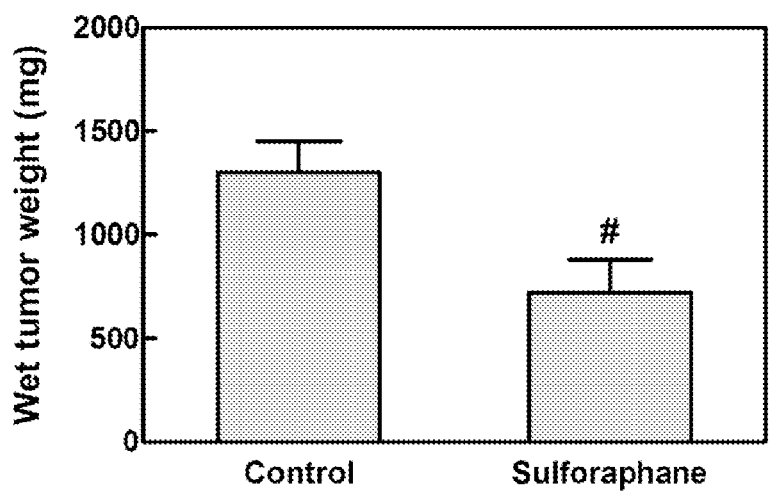
Figure 6C:
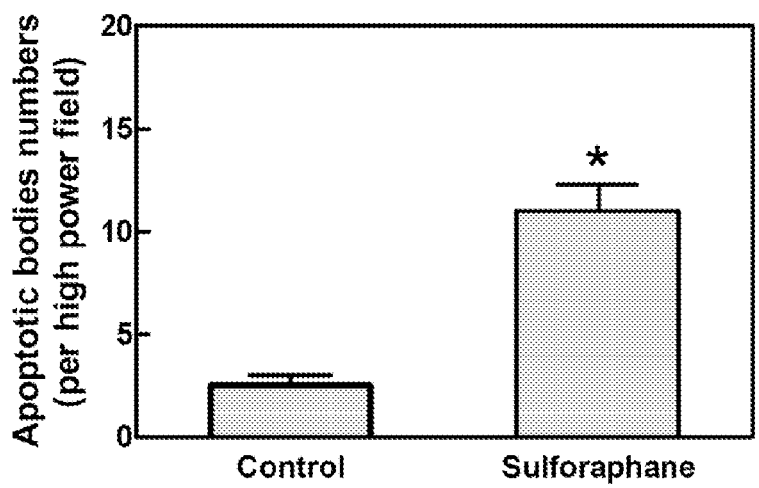

In vivo studies were conducted to testify whether SFN administration affects growth of SK-MEL 31 xenografts in nude mice. Effect of oral administrated SFN on SK-MEL 31 xenografts growth was determined in two independent experiments. SFN treatment caused a significant inhibition of SK-MEL 31 xenograft growth. At 16 days after tumor implantation, the average tumor volumes in control and SFN-treated mice were 310.5±113.3 and 154.4±95.4 mm³ respectively, reflecting a 50% reduction in tumor volume in SFN group (p<0.01, FIG. 6A). Similar statistically significant inhibition of SK-MEL 31 tumor xenograft growth after oral administration of SFN was observed in the second independent experiment. Tumor wet weight comparison showed significant decrease in the SFN treated group (p<0.01, FIG. 6B). TUNEL assay revealed ~4.4 fold higher count of apoptotic bodies in tumor sections from SFN-treated mice than in controls (p<0.05, FIG. 6C).

Example 7

Bcl-2 Family Protein Level Changes in SFN-Induced Apoptosis

Figure 7A:
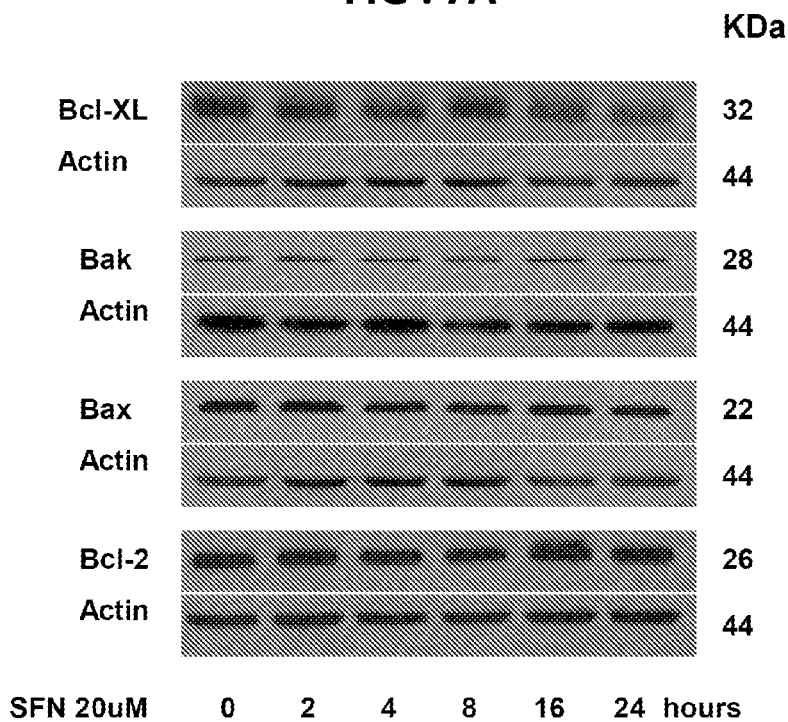
FIGS. 7A-7B are a set of digital images demonstrating expression of Bcl-2 family using lysates from SK-MEL 31 cells exposed to 20 μM SFN for specified time intervals; and expression of IAPs and Smac, cytochrome c released from mitochondria after SFN treatment.

To explore the mechanisms of SFN induced apoptosis in SK-MEL 31 cells, the effect of SFN treatment on expression of Bcl-2 family of anti-(Bcl-2 and Bcl-XL) and pro-apoptotic (Bax and Bak) proteins was determined. Representative Western blots illustrating the effect of SFN treatment on Bcl-2 family protein level are shown in FIG. 7. Exposure of SK-MEL 31 cells to 20 μM SFN resulted in down-regulation of Bcl-XL, that was evident from the 2 hour time point (FIG. 7A). No marked change of Bcl-2 was identified, and Bax and Bak expression was observed at all time points investigated.

Example 8

Involvement of Caspases in SFN-Induced Apoptosis

Figure 8A:
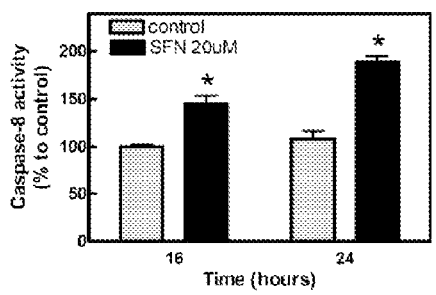
FIGS. 8A-8E are a set of bar graphs (A, B and D) and a set of digital images (C and E) demonstrating involvement of caspases in SFN induced apoptosis in SK-MEL 31. (A) and (B): Colormetric assays of caspase-8 and caspase-9 activity after SFN treatment for 16 and 24 hours; the caspase activity was presented as the percentage of control group. (C) Western blot analysis for cleaved caspase-3, caspase-8 and caspase-9 using lysates from SK-MEL 31 cells exposed to 20 mM SFN for specified time intervals (equal amounts (60 μg) of lysate protein subjected to gel electrophoresis). (D) ELISA detection of cytoplasmic histone associated DNA fragments level after introduction of caspase inhibitors before SFN treatment. (E) Western blot assay of caspase-3 cleavage after introduction of caspase inhibitors before SFN treatment. All experiments were repeated twice and results were comparable. Data are mean±SE of three determinations in (A), (B), (D) from a representative experiment. The notation (*) indicates a significantly different compared with control (caspase activity assay) or SFN treated group (cell Death ELISA) ($p<0.01$) by one-way ANOVA.
Figure 8B:
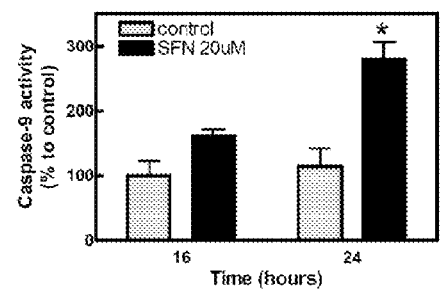
Figure 8C:
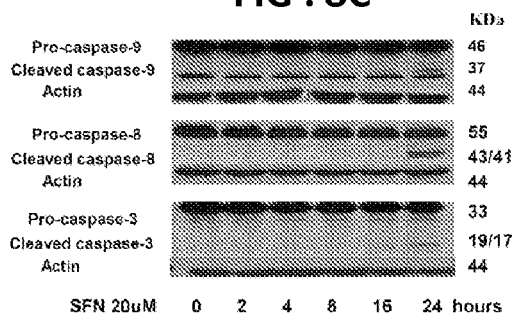
Figure 8D:
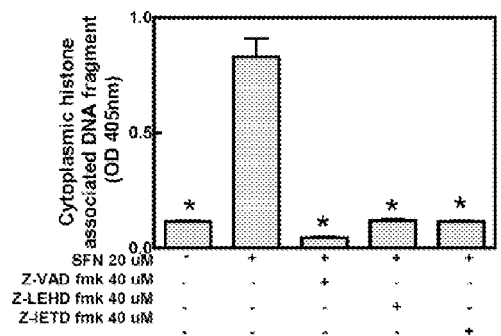
Figure 8E:
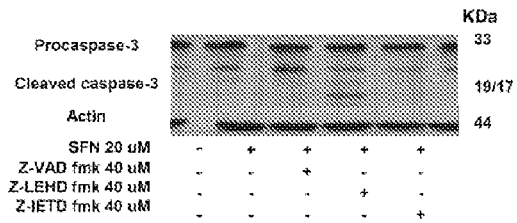

Caspases are aspartate-specific cysteine proteases that play critical roles in apoptosis. Activation of caspases results in cleavage and inactivation of key cellular proteins, including the DNA repair enzyme PARP. Activation of caspases after SFN treatment was evaluated by immunoblot for cleaved caspase-8, -9 and caspase-3, and the caspase-8, 9 activity changes with colormetric assay kits. Treatment of SK-MEL 31 cells with 20 μM SFN resulted in cleavage of procaspase-9, procaspase-8 and procaspase-3 as evidenced by appearance of intermediates (37 KDa for caspase-9, 43/41 KDa for caspase-8 and 19/17 KDa for caspase-3) at the 24 hour time point (FIG. 8C). Treatment with 20 μM SFN significantly induced a caspase-8 activity increase, specifically 45% (16 hour) and 73% (24 hour) increase compared with the control group, with a 148% increase in caspase-9 activity at 24 hours (p<0.05, FIGS. 8A-8B). To confirm the involvement of caspases in the SFN induced apoptosis in SK-MEL 31 cells, inhibitors for general caspase (z-VADfmk) and caspase-8 (z-IETDfmk), caspase-9 (z-LEHDfmk) were introduced to block the corresponding caspase activity. Incubation with the caspase inhibitors significantly lowered the SFN induced cytoplasmic histone associated DNA fragments level in Cell Death ELISA assay (p<0.05, FIG. 8D). Western blot of cleaved caspase-3 showed blockage of caspase-3 cleavage after introduction of caspase inhibitors before SFN exposure (FIG. 8E).

Example 9

Other Apoptosis Regulating Proteins Involved

Figure 7B:
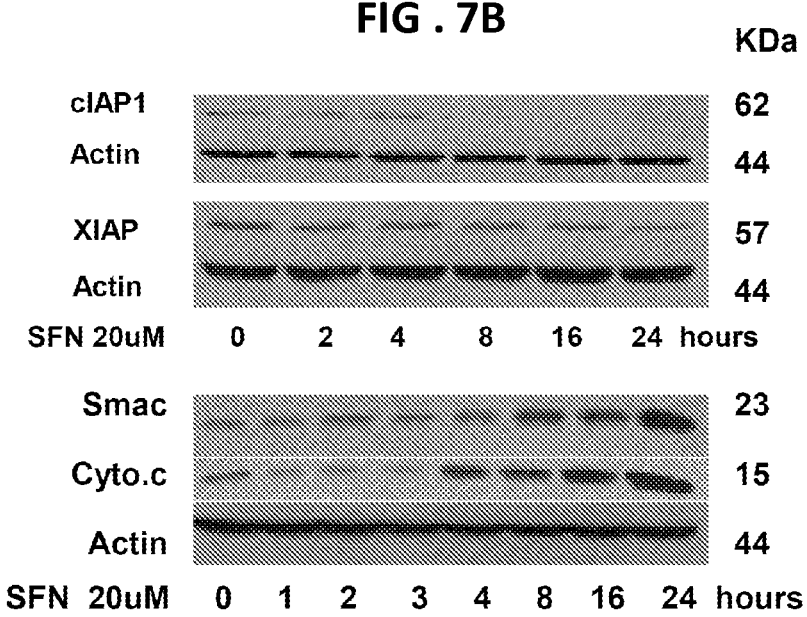
Figure 9A:
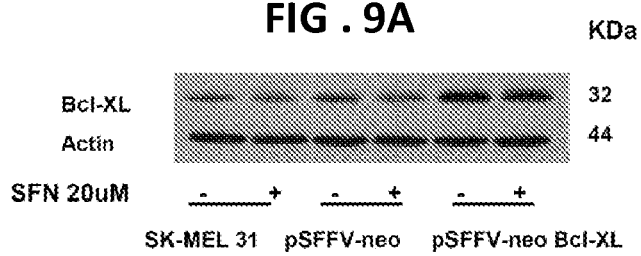
FIGS. 9A-9E are a set of digital images (A, C, D and E) and a bar graph (B) demonstrating that Bcl-XL overexpression protects against SFN induced cell apoptosis. (A) shows immunoblotting for Bcl-XL using lysates from S-KMEL31 cells transiently transfected with pSFFV-Bcl-XL and pSFFV-neo plasmids. (B) shows ELISA detection of cytoplasmic histone associated DNA fragments level in SK-MEL31, SK-MEL31/neo and SK-MEL 31/Bcl-XL cells following exposure to SFN 10 μM for 24 hours. Data are mean±SE, n=3. The results are significantly different compared with control, with the notation (*) signifying significance at $p<0.01$ and the notation (#) indicating significance at $p<0.05$ by one-way ANOVA. (C) shows cleavage of PARP after exposure to SFN 20 μM for 24 hours. (D) shows cleavage of pro-caspase 3 and 9 after exposure to SFN 20 μM for 24 hours. (E) shows release of cytochrome-c and Smac from mitochondria after exposure to SFN 20 μM for 24 hours.
Figure 9B:
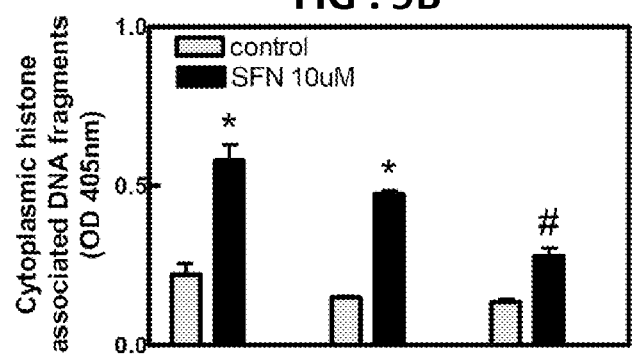
Figure 9C:
Figure 9D:
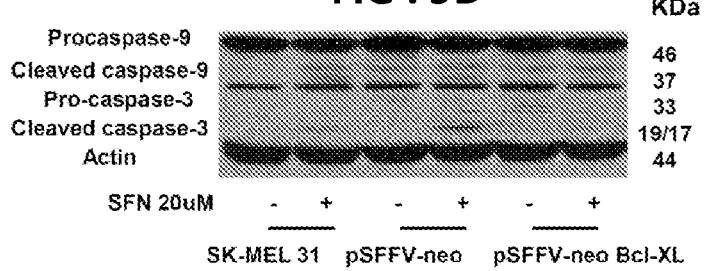
Figure 9E:
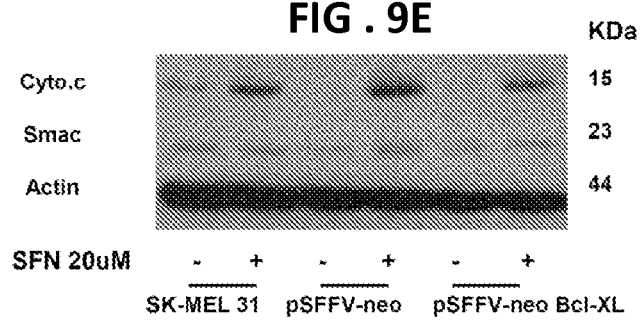

There are many proteins other than caspases that take part in apoptosis. Some of these protein level changes after SFN exposure were determined to examine their role in SK-MEL 31 cell apoptosis. IAPs are a group of proteins that exert inhibitory effect on cellular apoptosis through different pathways, and treatment with SFN caused consecutive cIAP1 and XIAP level decreases with time increasing (FIG. 7B). Smac/DIABLO and cytochrome c are small molecules released from mitochondria upon the disruption of the mitochondrial membrane integrity, which exert their pro-apoptic activity through interaction with other molecules. The cytosolic levels of Smac and cytochrome c showed time-dependent increases after SFN incubation, with significantly increases occurring after 8 hours for both Smac and cytochrome c (FIG. 9E).

Example 10

The Protective Role of Bcl-XL Against SFN Induced Apoptosis

It was shown consistently that Bcl-XL was down-regulated after exposure to SFN. To determine the exact role of Bcl-XL in SFN induced apoptosis, SK-MEL 31 cells were transiently transfected with pSFFV-Bcl-XL and pSFFV-neo (vector), and assayed for the effect of Bcl-XL over-expression on SFN induced apoptosis and associated molecular changes. FIG. 9A shows the increased level of Bcl-XL in pSFFV-Bcl-XL transfected cells, but not in the vector transfected cells. Over-expression of Bcl-XL partially blocked the apoptosis induced by SFN (p<0.01, FIGS. 9B-9C). This effect was associated with decreased release of Smac and cytochrome-c into cytoplasm (FIG. 9E), and decreased activation of caspase-9 and -3 (FIG. 9D).

The data presented here showed that SFN efficiently suppressed the proliferation of SK-MEL 31 human melanoma cells in culture and also in animal experiments. Oral administration of SFN also retarded the growth of SK-MEL 31 xenografts in nude mice significantly. No side effect was observed in mice (no obvious weight loss, or organ weight difference between treated groups) at the doses used.

Figure 10:
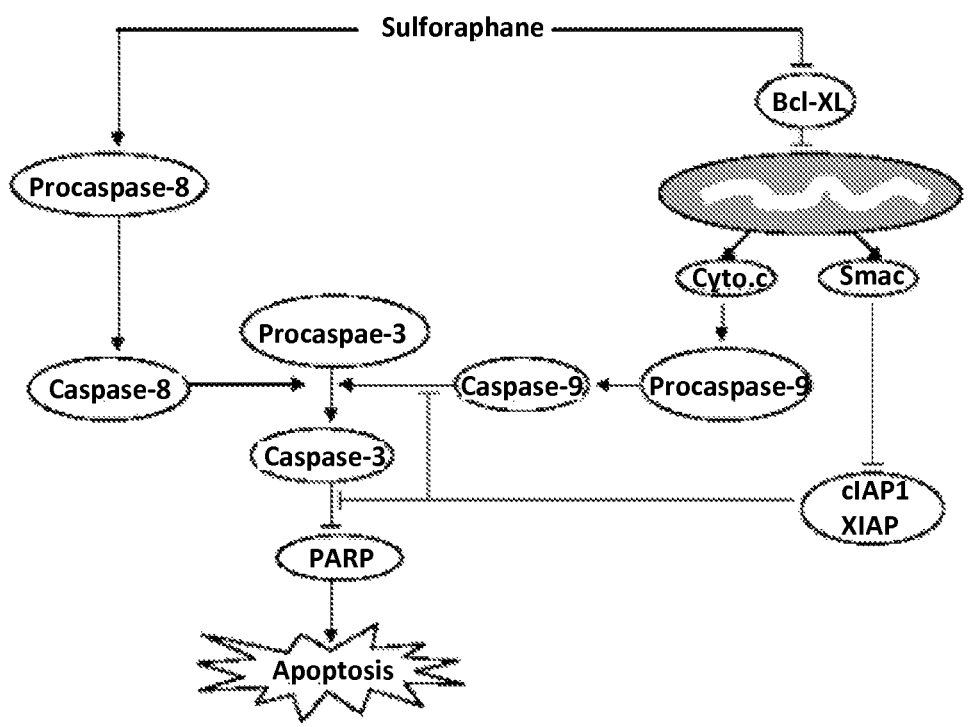
FIG. 10 is a flowchart demonstrating a proposed mechanism for SFN induced apoptosis in in SK-MEL 31 cells based on the results. SFN induced apoptosis in SK-MEL 31 cells was associated with a downregulation of anti-apoptotic Bcl-2 family members (Bcl-XL), IAPs (XIAP, cIAP1). Activation of caspase-8, -9, -3, and cleavage of PARP were also involved in this process. Release of cytochrome c and Smac into the cytoplasm suggests the role of mitochondria in apoptotic signaling.

The current results indicate that apoptosis induction is a major mechanism of the anti-proliferative effect of SFN both in cultured SK-MEL 31 cells and SK-MEL 31 xenograft in nude mice. Apoptosis is one of the most potent defenses against cancer, and it is often deregulated in cancer, which makes it a good target for cancer prevention. Without being bound by theory, an apoptosis inducing mechanism for SFN in SK-MEL 31 is shown in FIG. 10. Traditionally, apoptotic signaling pathways have been divided into the death receptor-mediated extrinsic pathway and mitochondria-mediated intrinsic pathway. Both were shown to be involved in the SFN induced apoptosis in SK-MEL 31 cells. It was also found that SFN induced apoptosis is associated with down-regulation of anti-apoptotic Bcl-2 family members: Bcl-XL, but not Bcl-2, and no significant level changes of Bax and Bak were observed, which are pro-apoptotic Bcl-2 family members. Without being bound by theory, the release of cytochrome c and Smac suggests the active involvement of mitochondria in apoptosis induction, while the decrease of XIAP and cIAP1 level at an early time point suggests their inhibitory effects were abrogated to facilitate apoptosis. See Li et al., Cell (1997) 91: 479-489; Du et al., Cell (2000) 102: 33-42; and Deveraux et al., EMBO (1998) 17: 2215-2223. Even though no up-regulation of Bax and Bak was observed, the consistent down-regulation of Bcl-XL and the fact that over-expression of Bcl-XL protected against SFN induced apoptosis suggest that the increased ratio of pro-/anti-apoptotic molecules resulted in activation of mitochondrial pathway. These changes form a complete caspase-activating cascade, leading to the activation of initiator caspase (caspase-9) and executioner caspase (caspase-3) and subsequent apoptotic changes (cleavage of PARP and appearance of cytoplasmic histone associated DNA fragments and condensed nucleus). See Thornberry et al., Science (1998) 281: 1312-1316; and Wolf et al., J. Biol. Chem. (1999) 274: 20049-20052. The cleavage of procaspase-8 and apoptosis blocking effect of caspase-8 specific inhibitor suggest the active role of caspase-8 mediated pathway in SFN induced apoptosis in human melanoma cells. This also indicated that there was significant $G_2/M$ phase cell cycle arrest, as shown by the FACS assay of cellular DNA content, which also account for the proliferation inhibition both in vitro and in vivo.

In conclusion, cultured SK-MEL 31 human melanoma cell and xenograft in nude mice are highly sensitive to growth inhibition by SFN, and apoptosis induction is one of the key mechanisms for this effect.

Example 11

SFN's Effect on Progression of Atypia in Nevi, a Clinical Trial

Sulforaphane (SFN) modulates progression of atypia in nevi. SFN affects the expression of STAT proteins in melanocytic and stromal elements of atypical nevi, which are precursor lesions and risk markers of melanoma. In this exemplary protocol, eighteen individuals in total receive oral SFN (SFN) standardized for 3 different concentrations of actual SFN content. Three groups of six subjects are randomly assigned to receive oral SFN at dosages of 50 µM, 100 µM, or 200 µM daily. Due to the established safety of SFN at all of the relevant dosage levels, no lower dosage level is completed prior to escalating to the next higher dosage level; i.e., subjects are randomized across all of the SFN dosage levels.

Eligibility Criteria

Subjects have at least two atypical nevi of >4 mm diameter and prior diagnosis of melanoma.

Subjects are ≥age 12.

Subjects do not have known allergies to cruciferous vegetables.

Subjects agree to abstain from dietary sources of glucosinolates and isothiocyanates beginning three days prior to the protocol and throughout duration of the active protocol (28 days).

Subjects are non-smokers for at least 6 months as smoking is found to interfere with the measurement of SFN metabolites.

Female subjects are not pregnant or breast feeding prior to and during course of the protocol.

Subjects meet Grade I criteria for complete blood count and complete metabolic panel as specified in the Common Toxicity Criteria (CTC) established by the National Cancer Institute (NCI) to be eligible for the protocol.

Protocol

Figure 11:
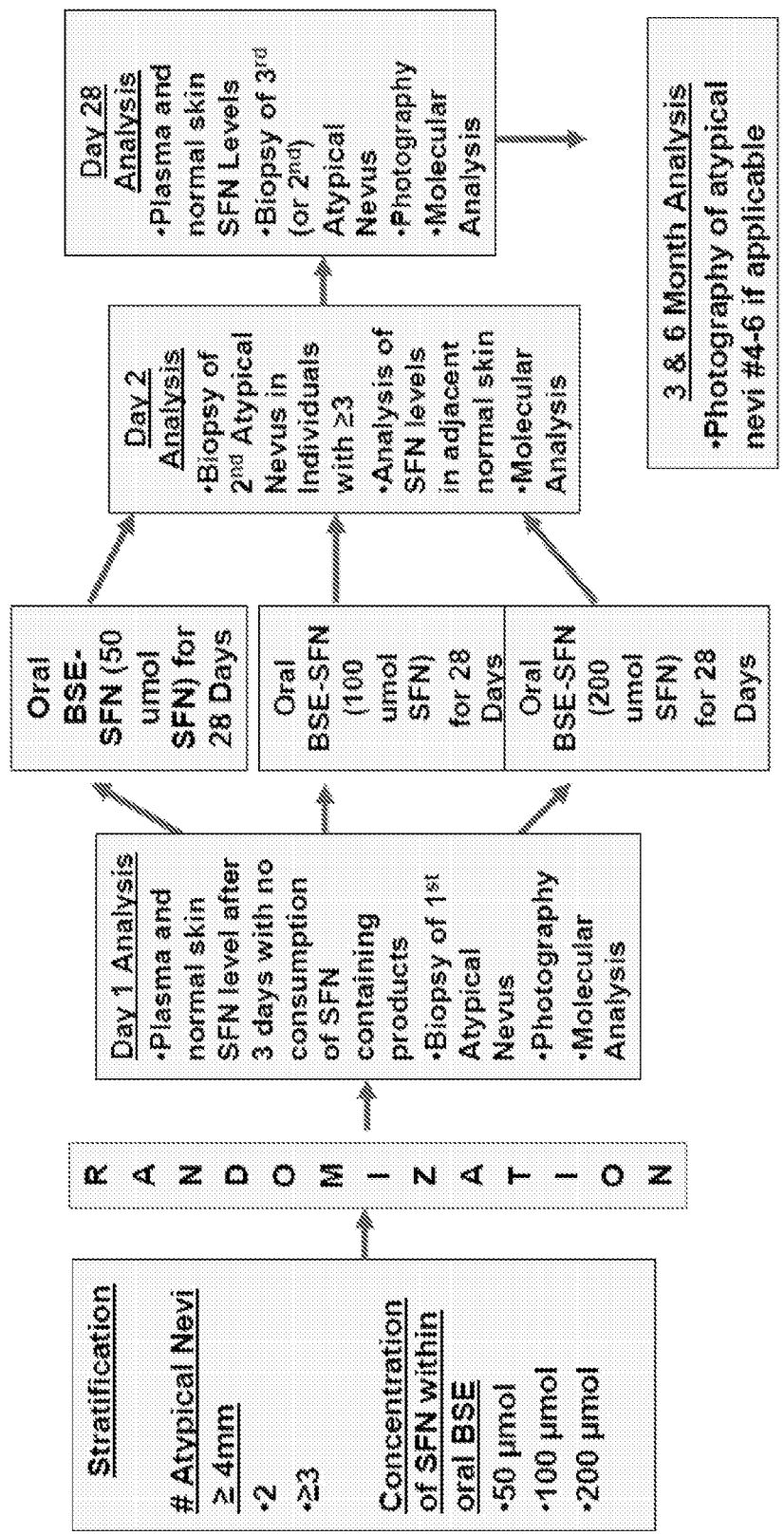
FIG. 11 is a schematic diagram of an exemplary protocol for the administration of SFN to a subject with atypical nevi.

The protocol is conducted as follows and as shown in FIG. 11:

Identify 2-6 atypical nevi from eligible individuals and label "A-F" based on degree of atypia.

Obtain biopsy (excisional or large punch) of an atypical nevus by random selection at protocol onset to act as control and assess the degree of atypia by histopathological and photographic examination and evaluate the levels of STAT 1, STAT3 at baseline prior to SFN administration. Obtain an adjacent tissue biopsy of normal skin and plasma sample at protocol onset to establish baseline SFN levels.

SFN is orally administered to the protocol population in 3 randomly assigned dosage groups (50, 100, and 200 µM daily) for 28 days (4 weeks), as shown in FIG. 11. Following 27 days of SFN administration (i.e., protocol day 28), plasma samples, photography of index designated atypical nevi, and biopsy of selected atypical nevi and surrounding normal skin are obtained, as shown in FIG. 12. These data provide for assessment of:

Concentration of SFN in normal skin through mass-spectrometric analysis.

Degree of atypia in nevi through histopathologic and photograph analysis.

Level of STAT 1 and STAT3 expression within atypical nevi.

For individuals with >3 atypical nevi an additional atypical nevus is biopsied and analyzed in similar fashion as above on day 2 of the protocol, 24 hours following first administration of BSE-SFN.

The three dosing groups are analyzed for:

Any change in the clinical or histological features of atypia observed when comparing pre- and post-SFN administration nevi.

Optimal dose of SFN to be utilized based on SFN concentrations measured within normal skin and plasma and effects on STAT expression levels and nevus histology.

The modulation of STAT expression levels between control (pre-administration) and post-SFN-administration nevi in each group.

Exam and Lesion Selection

An entry clinical exam is performed within two weeks of enrollment in the protocol, and the clinical features and number of nevi are recorded by anatomic site. Any nevi or lesions with possible question of incipient melanoma are removed prior to the protocol. Prior to drug administration up to six atypical nevi ≥4 mm are photographed and ranked morphologically (visually) for atypia, with "A" being the most atypical and "F" the least atypical. Analysis of nevi varies depending on if an individual has 2, 3, or ≥4 atypical nevi available for analysis as follows:

1. Individuals with 2 Atypical Nevi

One nevus is randomly selected for photographic documentation and removal for histological and molecular evaluation prior to SFN administration and serves as a control. The second nevus is marked for follow-up photography and biopsy evaluation, and photographed (or tattooed with India ink) for localization in the event of clinical involution or change after 28 days of SFN administration. After 28 days of SFN administration the second nevus is biopsied to perform routine histological as well as STAT and SFN expression and immunohistological studies.

2. Individuals with 3 Atypical Nevi

With the addition of a third atypical nevus, that nevus is biopsied at 24 hours following first administration of oral SFN and subsequent histological and molecular evaluation similar to nevus biopsied at day 28.

3. Individuals with 4 or More Atypical Nevi

The remaining nevi (one, two or three nevi) designated to be analyzed are evaluated at scheduled follow-up visits on day 28, 3 months, and 6 months. Note that these lesions are evaluated observationally; i.e., they are not biopsied for the purpose of this clinical investigation.

Photography Session

Subjects undergo photographic documentation of index nevi with macrophotography performed upon each nevus using a reference measurement and white balance tape prior to its removal, as well as at the start of the protocol. The selected atypical lesions are photographed for documentation at a fixed magnification of 1:10 and 1:2 under standard lighting conditions. Measurement tapes for size, date of photograph, and the type of lesion identified are included on all photographs and also recorded on a flow sheet for reference.

Lesions are identified and coded in a protocol form for evaluating nevi according to location, symmetry, border, color, size, and descriptive characteristics. All atypical lesions are photographed at time of selection and after SFN administration prior to excision.

Subjects are asked to have their nevi photographed with the use of a dermatoscope. The dermatoscope is a small handheld optical instrument that is used to visualize skin lesions. It has a 10× magnifying lens and uses 6 LED lights for transillumination. The glass lens is applied directly to the subject's skin and photographs are taken with an attached digital camera. No heat or ultraviolet radiation is generated that could burn or harm the subject. The specific instrument used in this protocol is the Heine Delta 20 Dermatoscope.

SFN Administration

A total of 18 subjects are studied with random assignment of 6 individuals to each of three groups that vary according to the dose of SFN at 50, 100, and 200 μM, respectively. The SFN is taken once daily at 10 am±2 hours prior to other foods and fluids. Subjects are asked to fast on day 0 (day prior to biopsy and SFN administration) and day 27 after midnight in order to limit the effect food may have on analysis of SFN pharmacokinetics. Individuals with >3 atypical nevi are asked to fast after midnight on day 1 as well in preparation for biopsy of an additional atypical nevus on day 2, 24 hours following first administration of SFN. On day 1 oral SFN is provided following biopsy in the clinic. On days 2 (when applicable) and 28 of the protocol, each subject takes the prescribed dose of oral SFN at 10 am±2 hours in the clinic of the attending oncologist, surgeon or dermatologist. Biopsies of atypical nevi and biopsies of adjacent normal skin are obtained at 2 hours±30 minutes.

Follow-Up Procedures

Surveillance photography of atypical nevi for individuals who had between 4-6 lesions being followed at protocol onset is performed at 3 and 6 months, as shown in FIG. 12.

Collection of Blood Specimen

Individuals are required to undergo phlebotomy to assess pre- and post-administration SFN levels in plasma. On day 1 of the protocol, a blood sample is drawn prior to administration of oral SFN to serve as a control for SFN level. A second blood sample is drawn 2 hours±30 minutes following administration of SFN to measure SFN concentration within plasma. On day 28, a blood sample is drawn prior to that day's SFN dose and again 2 hours±30 minutes following the dose to assess SFN concentration in plasma.

Biopsy of Atypical Nevi and Adjacent Normal Skin

On days 1 & 2 (when applicable), and day 28 of the protocol, separate biopsies of designated atypical nevi and surrounding normal skin are obtained 2 hours±30 minutes following administration of the morning SFN dose at 10 am±2 hours. Excised atypical nevi are submitted for routine and investigational histopathologic analysis, with a portion set aside for immunohistological and other evaluations of STAT signaling and for evaluation of the molecular and cellular features of each lesion, while biopsy of normal skin is analyzed for SFN concentration via mass spectrometry. Normal skin (after collection to be frozen at −80° C.) is utilized to measure SFN concentration so that the adjacent nevus is analyzed in its entirety for the routine and special staining of molecular and cellular features of interest. Normal skin sample for each individual is obtained either from the non-melanocytic tail from an excised atypical nevus or through a second biopsy near the site of one of the atypical nevi selected at random. Immediately upon removal, nevi are immersed in saline solution and preserved on ice. Specimens are sent for evaluation. Evaluators examine the lesion for gross and microscopic features and evaluate the synoptic factors relevant for atypical nevi; pathologists make the determination of the amount of tissue that is in excess of that necessary to establish the histological diagnosis of the lesion. The remaining tissue, if any, is snap frozen in liquid nitrogen and is used for molecular and immunologic analyses after completion of the pathological assessment of the nevus. This remaining tissue is available to a pathologist if needed for any question in regard to the routine pathological assessment of the skin lesion.

Analysis of SFN Pharmacokinetics

At onset on day 1, blood samples are obtained 2 hours±30 minutes following SFN administration and initial measurement of SFN level within plasma are recorded. Levels should be negligible if subjects refrained from consuming Brassica containing food and supplements for three days prior. SFN levels are measured again on day 28, 2 hours±30 minutes after final administration of oral SFN.

Measurement of STAT 1 and STAT 3 Expression

Immunohistochemistry is utilized at the onset of investigation and for the post-SFN administration samples to assess levels of STAT1 and STAT3 expression in control lesions and in nevi post-SFN exposure on day 28 and also day 2 for individuals with 3 or more atypical nevi. Analysis of the level of STAT expression is assessed independently by two separate pathologists. The ×20 objective on microscopy is used to evaluate the whole section in both pre- and post-administration samples. Pathologists are blinded to each sample, not knowing ahead of time if it is a pre- or post-administration sample they are viewing.

Quantification is decided by consensus of the two pathologists and a research faculty member. The percentage of cells with positive staining is evaluated for all samples. Cells with staining intensity 1+ to 4+ are considered positive; cells without staining (intensity 0) are considered negative. If the percentage of stained cells is less than 1%, it is considered zero.

Measurement of Gross Morphologic Response

Subjects undergo photography at baseline and day 28. Three investigators evaluate pre- and post-administration photographs in a blinded manner, to score the features of lesional atypia. Paired photographs in random blinded order of each nevus from two time points are evaluated for changes in overall shape and size, color, border, as well as macular and popular component. Loss of intensity of pigmentation or features of asymmetry, border irregularity/diffusion, color variegation, or diminution in size are taken as signs of reduction of atypia. Nevi revealing increases in asymmetry, border irregularity/diffusion, color variegation, and size are deemed to have increased in morphologic atypia. For each subject, each pair of nevi is compared according to the defining features: size, asymmetry, color irregularity and border indistinctness. For each feature, the most atypical nevus of the two are selected and recorded (with scoring ties indicated). For individuals with ≥4 atypical nevi, the three remaining non-biopsied nevi are followed routinely at day 28, 3 months and 6 months.

Measurement of Histologic Response

The atypia/dysplasia score of lesions is judged on the grounds of pre-specified categories of architectural and cytologic atypia and is determined for lesions removed at the outset of the protocol and again at the completion of 28 days of oral SFN administration. The pathologist remains blinded as to the date and time of administration for scoring evaluations. A portion of the excised nevus is snap-frozen for future research studies, while the portion of the specimen deemed necessary for pathological assessment by the triage pathologist is submitted for routine histological examination.

Measurement of Molecular Expression/Response

Preclinical studies indicate that SFN induces apoptosis and cell cycle arrest in melanoma cells. Therefore, non-exposed and SFN-exposed nevi are evaluated for evidence of apoptosis (via in situ TUNEL Assay) and cellular proliferation (via Ki-67 immunostaining). Additionally, alterations in gene expression profiles of the atypical nevi are assessed through application of cDNA microarray technology.

Protein Expression Array Analysis

Biopsy tissues obtained during the course of this protocol, before and after SFN administration, beyond those required for the above studies are banked and used for oligonucleotide, DNA, RNA and protein expression array analysis to explore differences that may be associated with SFN administration, and the immunological and molecular features of progression in melanocytic nevi.

These blood and tumor biopsy samples are stored in a tissue bank. Samples to be analyzed for expression array differences are de-identified and are retained.

Drug composition

Active Drug Substance: Sulforaphane (SFN)

Other Names: 1-isothiocyanato-4-(methylsulfinyl)-butane

Classification: Isothiocyanate

Mode of Action: SFN is an inhibitor of phase 1 enzymes and leads to reduction in carcinogen activation due to inhibition of cytochrome P450 dependent monooxygenases. SFN also is a potent inducer of phase 2 enzymes, such as glutathione transferases, and leads to accelerated carcinogen detoxification. Preclinical studies demonstrate that SFN induces apoptosis and cell cycle arrest in tumor cells.

Storage and Stability: The prepared oral composition (gel capsules) of SFN are stored in a freezer at $-20°$ C.

Preparation: 3-Day-old broccoli sprouts are extracted with hot water, treated with daikon and freeze dried under good manufacturing conditions to prepare gel capsule compositions of SFN containing 50, 100 and 200 $\mu$mol of SFN.

Administration: Daily oral dosing of SFN standardized for SFN at specified dosages prepared in gel-capsules, provided by Drs. Jed W. Fahey and Paul Talalay from Johns Hopkins University.

Statistical Considerations

This protocol evaluates the effects of SFN on atypical nevi. The objectives of this protocol include evaluating the safety profile of SFN, quantifying the effects (and the corresponding variation of the measurements) of oral SFN, and documenting the PK (pharmacokinetics) and PD (pharmacodynamics) of SFN administered at different SFN dose levels for subjects with a history of melanoma and atypical nevi. A total of 18 subjects in 3 cohorts of 6 subjects each with at least two atypical nevi are randomly assigned to receive oral SFN at SFN doses of 50, 100, or 200 $\mu$M daily. Up to a total of 3 nevi is dissected from the subjects for the protocol. To ensure that each arm of the study contains roughly the same number of subjects with various numbers of atypical nevi in total, the randomization is stratified by the number of atypical nevi on the skin of the subject (2, 3, or 4 and above). Nevi are randomized within the same subject to determine which is dissected before and after SFN administration:

Up to 6 nevi are studied within the same subject. The nevi are labeled with "A", "B", "C" to up to "F" based on the morphological measurement of the severity of disease. A random sequence of the letters is generated for each subject by the protocol statistician with regard to the order of the nevi taken out.

For subjects with 2 index atypical nevi, one is randomly chosen to dissect before the SFN administration to serve as control and the other nevus to be sent for analysis.

For subjects with 3 or more nevi, three of them are randomly chosen and dissected at baseline and at approximately 24 hours and 28 days. The random order of dissection is decided by the protocol statistician as disclosed above. The remaining 1-3 nevi are analyzed by clinical and photographic analysis at day 28, 3 months, and 6 months. Subsequent evaluations of these nevi are as per the standard clinical care of these subjects.

The photographic documentation and measurements of the atypical nevi and expression of protein markers is measured for the dissected nevi. The randomization procedure for the order to be dissected, as disclosed above, ensures that nevi dissected before and after administration are comparable.

The endpoints of the protocol include:

Photographic outcomes including size of lesion, border changes, color changes,

STAT1 and STAT 3 protein level measured by IHC,

Other protein marker levels measured by high-throughput multiplex assays, and

Pharmacokinetics outcomes at each dose level.

Analysis Plan for Efficacy Endpoints

The analysis of this protocol focuses on estimation of mean (and/or median) and variation of the endpoints at both baseline and post SFN administration dissections.

The endpoints of interests are either continuous (e.g. nevus surface size, margin, pigmentation) or ordinal (e.g. IHC measure of protein level). For continuous variables, the mean (with 95% confidence interval), median and variance at each time point for each protocol arm is calculated. Histogram and boxplots are also used to evaluate the distribution of each variable. The difference of each variable at a specific post SFN administration time point from the baseline level is used as the measurement of investigational treatment effect. Similar descriptive analysis disclosed above is done for this quantity for each dose group. For ordinal variables, the range and the median of the variable before and after the SFN administration for each protocol arm is calculated. Bar plots and contingency tables are used to describe the distribution of each ordinal variable. The Wilcoxon signed-rank test is used to compare the pre- and post-SFN administration values of each variable. A generalized linear mixed effect model with random intercept, which accounts for the clustering effect at the subject level, is used to explore the effects of the SFN administration and the SFN dose level on each outcome of interest.

A subset of the subjects have up to 3 nevi followed observationally for an extended period of time. Trajectory plots are used to evaluate the morphological changes over time for these nevi. A paired t-test is used to test the SFN administration effect at each time point. A linear mixed effect model is used to evaluate the SFN administration, SFN dose, and time effect on the morphological changes of the nevi.

Sample Size Justification

Table 2 provides the 80% exact confidence intervals for SAE (small area estimate) rate for different possible outcomes of each arm.

TABLE 2

| 90% Confidence interval (CI) estimates for SAE rate | | |
|---|---|---|
| Number of SAEs observed | SAE rate estimate | 80% exact CI |
| 1/6 | 17% | (2%, 51%) |
| 2/6 | 33% | (9%, 67%) |
| 3/6 | 50% | (20%, 80%) |

The analysis unit for this protocol is the nevus. Each subject contributes from 2 to 3 nevi to the overall analysis. Therefore, the study has a minimum of 6 nevi at the baseline and day 28 time points for each arm of the study. With 6 nevi, the mean of each outcome is estimated with an 80% CI width equal to 1.2 times the standard deviation of the corresponding outcome.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method of reducing progression of atypical nevi in a subject, comprising administering orally to a subject having atypical nevi a therapeutically effective amount of a pharmaceutical composition comprising sulforaphane, thereby reducing progression of the atypical nevi.

2. A method of treating a melanoma in a subject, comprising administering orally to a subject a therapeutically effective amount of a pharmaceutical composition comprising sulforaphane, thereby treating the melanoma in the subject.

3. The method of claim 1, wherein reducing progression comprises reducing emergence of additional atypical nevi in the subject.

4. The method of claim 1, wherein reducing progression comprises reducing transition of atypical nevi from morphologically less atypical to morphologically more atypical on a tiered scale.

5. The method of claim 1, comprising administering the sulforaphane as a tea or as a gel capsule.

6. The method of claim 1, comprising administering about 50 to about 400 µM of sulforaphane.

7. The method of claim 1, comprising administering about 0.5 to about 10 µM of sulforaphane per kilogram of bodyweight of the subject.

8. The method of claim 1, comprising administering about 50, about 100, or about 200 µM of sulforaphane.

9. The method of claim 1, comprising administering about 0.5, about 2.0, or about 4.0 µM of sulforaphane per kilogram of bodyweight of the subject.

10. The method of claim 1, comprising administering the sulforaphane in repeated doses.

11. The method of claim 1, comprising administering the sulforaphane thrice daily, twice daily, daily, bi-weekly, or weekly.

12. The method of claim 1, wherein administering is repeated over about 10 days to about 6 months.

13. The method of claim 2, wherein the subject has a family history of melanoma or dysplastic nevi syndrome.

14. The method of claim 1, wherein the subject has two or more atypical nevi.

15. The method of claim 1, wherein the subject has two or more atypical nevi that are greater than 4 millimeters in diameter.

16. The method of claim 1, wherein the subject has two or more atypical nevi, and wherein one or more of the nevi have been morphologically classified on a tiered scale.

17. The method of claim 2, wherein the subject has a loss of function mutation in an MC1R gene.

18. The method of claim 1, further comprising measuring STAT1 or STAT3 expression in a sample from the subject.

19. The method of claim 18, wherein the sample is a biopsy.

20. The method of claim 19, wherein measuring STAT1 or STAT3expression comprises an immunoassay.

21. A method of inducing cell cycle arrest and/or apoptosis of a melanoma cell, comprising:
    administering orally to a subject a pharmaceutical composition comprising sulforaphane, thereby inducing cell cycle arrest and/or apoptosis of the melanoma cell; and
    measuring the cell cycle arrest and/or apoptosis of the melanoma cell.

22. The method of claim 2, wherein treating the melanoma comprises reducing transition of an atypical nevus of the melanoma from morphologically less atypical to morphologically more atypical on a tiered scale.

* * * * *